(12) United States Patent
Church et al.

(10) Patent No.: US 10,501,791 B2
(45) Date of Patent: Dec. 10, 2019

(54) SEQUENCING BY STRUCTURE ASSEMBLY

(71) Applicant: President and Fellows of Harvard College, Cambridge, MA (US)

(72) Inventors: George M. Church, Brookline, MA (US); Richard C. Terry, Carlisle, MA (US); Frederic Vigneault, Natick, MA (US); Francois Vigneault, Medford, MA (US)

(*) Notice: Subject to any disclaimer, the term of this patent is extended or adjusted under 35 U.S.C. 154(b) by 0 days.

(21) Appl. No.: 14/350,975

(22) PCT Filed: Oct. 12, 2012

(86) PCT No.: PCT/US2012/059873
§ 371 (c)(1),
(2) Date: Apr. 10, 2014

(87) PCT Pub. No.: WO2013/055995
PCT Pub. Date: Apr. 18, 2013

(65) Prior Publication Data
US 2014/0349294 A1    Nov. 27, 2014

Related U.S. Application Data

(60) Provisional application No. 61/609,990, filed on Mar. 13, 2012, provisional application No. 61/547,138, filed on Oct. 14, 2011.

(51) Int. Cl.
  *C12Q 1/68*     (2018.01)
  *C12Q 1/6869*   (2018.01)
  *C12Q 1/6874*   (2018.01)
  *C12Q 1/6876*   (2018.01)

(52) U.S. Cl.
  CPC ......... *C12Q 1/6869* (2013.01); *C12Q 1/6874* (2013.01); *C12Q 1/6876* (2013.01)

(58) Field of Classification Search
  USPC ....... 435/6.1, 6.11, 6.12, 91.1, 91.2; 436/94, 436/501; 536/23.1, 24.3, 24.33, 25.3
  See application file for complete search history.

(56) References Cited

U.S. PATENT DOCUMENTS

| | | | |
|---|---|---|---|
| 4,123,610 A | 10/1978 | Summerton et al. | |
| 4,981,985 A | 1/1991 | Kaplan et al. | |
| 5,563,056 A | 10/1996 | Swan et al. | |
| 5,830,708 A | 11/1998 | Naughton | |
| 7,323,305 B2 | 1/2008 | Leamon et al. | |
| 7,473,767 B2 | 1/2009 | Dimitrov | |
| 8,501,459 B2* | 8/2013 | Chen .................... | C12Q 1/6827 435/287.2 |
| 8,551,710 B2 | 10/2013 | Bernitz et al. | |
| 9,217,151 B2 | 12/2015 | Yin et al. | |

(Continued)

FOREIGN PATENT DOCUMENTS

| KR | 20080003402 A | 1/2008 |
|---|---|---|
| WO | 9746704 A1 | 12/1997 |

(Continued)

OTHER PUBLICATIONS

Office Action issued for corresponding European Patent Application No. 12780609.9, dated Sep. 23, 2015.

(Continued)

*Primary Examiner* — Frank W Lu
(74) *Attorney, Agent, or Firm* — Banner & Witcoff, Ltd.

(57) ABSTRACT

A method of sequencing nucleic acids is provided using sequencing by ligation and/or sequencing by hybridization.

15 Claims, 10 Drawing Sheets

Specification includes a Sequence Listing.

(56) References Cited

U.S. PATENT DOCUMENTS

| | | |
|---|---|---|
| 2002/0015952 A1 | 2/2002 | Anderson et al. |
| 2003/0148335 A1 | 8/2003 | Shen et al. |
| 2004/0077014 A1 | 4/2004 | Becker |
| 2004/0248144 A1 | 12/2004 | Mir |
| 2004/0259190 A1 | 12/2004 | Naughton |
| 2005/0106629 A1 | 5/2005 | McGrath et al. |
| 2005/0147981 A1 | 7/2005 | Yamakawa et al. |
| 2005/0233318 A1 | 10/2005 | Chee et al. |
| 2006/0024711 A1 | 2/2006 | Lapidus et al. |
| 2006/0177833 A1 | 8/2006 | Brenner |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2008/0176769 A1 | 7/2008 | Rank et al. |
| 2009/0005259 A1 | 1/2009 | Drmanac |
| 2009/0208965 A1 | 8/2009 | Tafas et al. |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0086774 A1 | 4/2011 | Dunaway |
| 2011/0092376 A1 | 4/2011 | Colston, Jr. et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2013/0017229 A1 | 1/2013 | Mooney et al. |
| 2013/0245096 A1 | 9/2013 | Abitbol |
| 2014/0087378 A1 | 3/2014 | Chatre et al. |
| 2014/0220587 A1 | 8/2014 | Green, Jr. et al. |
| 2015/0133319 A1 | 5/2015 | Fu et al. |
| 2016/0024555 A1 | 1/2016 | Church et al. |
| 2016/0265046 A1 | 9/2016 | Zhang et al. |
| 2017/0212983 A1 | 7/2017 | Cai et al. |

FOREIGN PATENT DOCUMENTS

| | | |
|---|---|---|
| WO | 01/26708 A1 | 4/2001 |
| WO | 2007086900 A2 | 8/2007 |
| WO | 2007/121489 A2 | 10/2007 |
| WO | 2008/069973 A2 | 6/2008 |
| WO | 2008069973 A2 | 6/2008 |
| WO | 2009/046149 A1 | 4/2009 |
| WO | 2009046149 A1 | 4/2009 |
| WO | 2010/080134 A1 | 7/2010 |
| WO | 2010080134 A1 | 7/2010 |
| WO | 2011/143583 A1 | 11/2011 |
| WO | 2012005595 A2 | 1/2012 |
| WO | 2012/058638 A2 | 5/2012 |
| WO | 2012/150035 A1 | 11/2012 |
| WO | 2012150035 A1 | 11/2012 |
| WO | 2013/055995 A2 | 4/2013 |
| WO | 2014/0163886 A1 | 10/2014 |
| WO | 2014/182528 A2 | 11/2014 |
| WO | 2015/118029 A1 | 8/2015 |

OTHER PUBLICATIONS

International Preliminary Report on Patentability issued from corresponding PCT/US2012/059873, dated Apr. 24, 2014.

Brenner Sydney et al: "Gene expression analysis by massively parallel signature sequencing (MPSS) on microbead arrays", Nature Biotechnology, Nature Publishing Group, New York, NY, US, vol. 18, No. 6, Jun. 1, 2000 (Jun. 1, 2000), pp. 630-634, XP002199492, ISSN: 1087-0156, DOI: 10.1038/76469.

Seo T S et al: "Four-color DNA sequencing by synthesis on a chip using photocleavable fluorescent nucleotides", Proceedings of the National Academy of Sciences, National Academy of Sciences, US, vol. 102, No. 17, Apr. 26, 2005 (Apr. 26, 2005), pp. 5926-5931, XP002353000, ISSN: 0027-8424, DOI: 10.1073/PNAS. 0501965102.

Dec. 18, 2014 (PCT) International Preliminary Report—App PCT/US2013/044241.

Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Eliscovich et al. mRNA on the move: The road to its biological destiny. Journal of Biological Chemistry, vol. 288, No. 28, pp. 20361-20368, Jul. 2013, in press May 2013 (Year: 2013).

Extended European Seach Report issued in corresponding European Application No. 12860433.7, dated Aug. 13, 2015.

Ginart, P et al. RNA Sequencing In Situ. Nat Biotechnol. Jun. 2014, vol. 32, No. 6; pp. 543-544; DOI: 10.1038/nbt.2921.

Grompe (1993) Nature Genetics DOI: 10.1038/ng1093-111.

Han et al. "Quantum-dot-tagged microbeads for multiplexed optical coding of biomolecules". Nature Biotechnology, vol. 19, 99. 631-635 (Jul. 31, 2001).

International Search Report and Written Opinion issued in corresponding International Application No. PCT/US2012/071398, dated Apr. 8, 2013.

International Search Report issued from corresponding PCT/US14/18580, dated Jul. 11, 2014.

Jambhekar et al. Cis-acting determinants of asymmetric, cytoplasmic RNA transport. RNA, vol. 13, pp. 625-642, 2007 (Year: 2007).

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).

Lee, Jh et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Mattin et al. Spatial expression of the genome: the signal hypothesis at forty. Nature Reviews. Molecular Cell Biology, vol. 12, No. 5, pp. 333-340, May 2011, Epub Apr. 2011. (Year 2011).

Meeks et al. Characterization of genes encoding poly(A) polymerases in plants: Evidence for duplication and functional specialization. PLoS One, vol. 4, No. 11, e8082, Nov. 2009, printed as pp. 1/10-10/10. (Year 2009).

Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year 2006).

Saliba, Ae et al. Single-Cell RNA-Seq: Advances and Future Challenges. Nucleic Acids Res. Jul. 22, 2014, vol. 42, No. 14; pp. 8845-8860; DOI: 10.1093/nar/gku555.

Seo, et al. Four-color DNA sequencing by synthesis on a chip using photocleavable fluorescent nucleotides. Proceeding of the National Academy of Sciences, Apr. 2005, 102 (17) 5926-5931.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

Singer-Kruger et al. Here, there, everywhere. RNA Biology, vol. 11, No. 8, pp. 1031-1039, Aug. 2014. (Year: 2014).

(56) References Cited

OTHER PUBLICATIONS

Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year 2004).

Weis et al. Protein targeting to subcellular organelles via mRNA localization. Biochimica et Biophysica Acta, vol. 1833, pp. 260-273, 2013, available online Apr. 2012 (Year 2012).

Thisse et al. 2008 Nature protocols vol. 3 No. 1 pp. 59-69. Doi:10.1038/nprot.2007.514.

Cao, Yi et al.,"In-situ immuno-PCR to detect antigens," The Lancet, Sep. 16, 2000, pp. 1002-1003, vol. 356.

Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].

Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.

Extended European Search Report dated May 13, 2019 for EP Application No. 16862929.3.

Extended European Search Report dated May 21, 2019 for European Application No. 16862945.9.

International Search Report and Written Opinion based on PCT/US2018/027583 dated Jun. 29, 2018.

Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.

Sano, Takeshi et al. "Immuno-PCR: Very Sensitive Antigen Detection by Means of Specific Antibody-DNA Conjugates," Science, Oct. 2, 1992, pp. 120-122, vol. 258.

Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.

Soderberg, Ola et al.,"Direct observation of individual endogenous protein complexes in situ by proximity ligation," Nature Methods, Dec. 2006, pp. 995-1000, vol. 3, No. 12, Nature Publishing Group.

\* cited by examiner

Base-calling Legend:
Circle (○) A (green channel)
Triangle (△) G (blue channel)
Square (□) T (red channel)

Base-calling Legend:
Circle (○) A (green channel)
Triangle (△) G (blue channel)
Square (□) T (red channel)

SEQUENCE LISTING

<160> NUMBER OF SEQ ID NOS: 42

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      sequencing primer

<400> SEQUENCE: 1
acccgtcagc cacta                                                      15

<210> SEQ ID NO 2
<211> LENGTH: 19
<212> TYPE: DNA
<213> ORGANISM: Artificial Sequence

```
<220> FEATURE:
<223> OTHER INFORMATION: Description of Artificial Sequence: Synthesized
      target sequence

<400> SEQUENCE: 2
tagtggctga cgggtatct                                                   19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe CY5 detectable moiety
<220> FEATURE:
<223> OTHER INFORMATION: Description of Combined DNA/RNA Molecule:
      Synthetic oligonucleotide probe CY5 detectable moiety
<220> FEATURE:
<221> NAME/KEY: modified_base
<222> LOCATION: (1)..(5)
<223> OTHER INFORMATION: a, c, t or g

<400> SEQUENCE: 3
nnnnnaucgt catgccaaac gt                                               22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe TR detectable moiety
<220> FEATURE:
<223> OTHER INFORMATION: Description of Combined DNA/RNA Molecule:
      Synthetic oligonucleotide probe TR detectable moiety
<220> FEATURE:
<221> NAME/KEY: modified_base
<222> LOCATION: (1)..(5)
<223> OTHER INFORMATION: a, c, t or g

<400> SEQUENCE: 4
nnnnncucgt catgccaaac gt                                               22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe FITC detectable moiety
<220> FEATURE:
<223> OTHER INFORMATION: Description of Combined DNA/RNA Molecule:
      Synthetic oligonucleotide probe FITC detectable moiety
<220> FEATURE:
<221> NAME/KEY: modified_base
<222> LOCATION: (1)..(5)
<223> OTHER INFORMATION: a, c, t or g

<400> SEQUENCE: 5
nnnnntucgt catgccaaac gt                                               22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe CY3 detectable moiety
<220> FEATURE:
<223> OTHER INFORMATION: Description of Combined DNA/RNA Molecule:
      Synthetic oligonucleotide probe CY3 detectable moiety
```

```
<220> FEATURE:
<221> NAME/KEY: modified_base
<222> LOCATION: (1)..(5)
<223> OTHER INFORMATION: a, c, t or g

<400> SEQUENCE: 6
nnnnngucgt catgccaaac gt                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe
<220> FEATURE:
<223> OTHER INFORMATION: Description of Combined DNA/RNA Molecule:
      Synthetic oligonucleotide probe
<220> FEATURE:
<221> NAME/KEY: modified_base
<222> LOCATION: (1)..(5)
<223> OTHER INFORMATION: a, c, t or g

<400> SEQUENCE: 7
nnnnncucgt gatatcagac gt                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe
<220> FEATURE:
<223> OTHER INFORMATION: Description of Combined DNA/RNA Molecule:
      Synthetic oligonucleotide probe
<220> FEATURE:
<221> NAME/KEY: modified_base
<222> LOCATION: (1)..(5)
<223> OTHER INFORMATION: a, c, t or g

<400> SEQUENCE: 8
nnnnntucgt ccaccaaaac gt                                              22

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe CY3 detectable moiety
<220> FEATURE:
<223> OTHER INFORMATION: Description of Combined DNA/RNA Molecule:
      Synthetic oligonucleotide probe CY3 detectable moiety
<220> FEATURE:
<221> NAME/KEY: modified_base
<222> LOCATION: (1)..(5)
<223> OTHER INFORMATION: a, c, t or g

<400> SEQUENCE: 9
nnnnngucgt tataccgt                                                   18

<210> SEQ ID NO 10
<211> LENGTH: 71
<212> TYPE: DNA
<213> ORGANISM: Artificial Sequence
<220> FEATURE:
<223> OTHER INFORMATION: Description of Artificial Sequence: Synthesized
      template oligonucleotide
```

```
<220> FEATURE:
<221> NAME/KEY: modified_base
<222> LOCATION: (20)..(55)
<223> OTHER INFORMATION: a, c, t or g

<400> SEQUENCE: 10
gttcctcatt ctctgaagan nnnnnnnnnn nnnnnnnnnn nnnnnnnnnn nnnnnacttc    60
agctgccccg g                                                         71

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 11
gttcctcatt ctctgaaga                                                 19

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 12
acttcagctg ccccgg                                                    16

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 13
atgaggaacc cggggcag                                                  18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      sequencing primer phosphorothioate bond

<400> SEQUENCE: 14
aatgaggaac ccggggcagc                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      sequencing primer phosphorothioate bond

<400> SEQUENCE: 15
aatgaggaac ccggggcagc                                                20
```

```
<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 16
gttcctcatt ctctgaaga                                                19

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 17
tcttcagaga atgag                                                    15

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 18
ccggggcagc tgaagt                                                   16

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 19
acttcagctg cc                                                       12

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 20
gttcctcatt ctctgaaga                                                19

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthesized
      template oligonucleotide biotin moiety

<400> SEQUENCE: 21
ccggggcagc tgaagt                                                   16
```

```
<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 22
gaagtcttct tactccttgg gccccgtcag acttc                              35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 23
gttccgagat ttcctccgtt gttgttaatc ggaac                              35

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthesized
      template oligonucleotide

<400> SEQUENCE: 24
taacaacaac ggaggaaa                                                 18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthesized
      template oligonucleotide phosphorothioate bond

<400> SEQUENCE: 25
acggggccca aggagtaag                                                19

<210> SEQ ID NO 26
<211> LENGTH: 71
<212> TYPE: DNA
<213> ORGANISM: Artificial Sequence
<220> FEATURE:
<223> OTHER INFORMATION: Description of Artificial Sequence: Synthetic
      template oligonucleotide
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (23)..(24)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: modified_base
<222> LOCATION: (32)..(33)
<223> OTHER INFORMATION: a, c, t or g
```

<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g

<400> SEQUENCE: 26
gttcctcatt ctctgaagan nanncnngnn tnnanncenn anntnngnnc nnannacttc    60
agctgccccg g                                                        71

<210> SEQ ID NO 27
<211> LENGTH: 71
<212> TYPE: DNA
<213> ORGANISM: Artificial Sequence
<220> FEATURE:
<223> OTHER INFORMATION: Description of Artificial Sequence: Synthetic
      template oligonucleotide
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (23)..(24)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g

<400> SEQUENCE: 27
gttcctcatt ctctgaagan ncnngnntnn anncnnggnn cnnanntnng nnannacttc    60
agctgccccg g                                                        71

<210> SEQ ID NO 28
<211> LENGTH: 71
<212> TYPE: DNA
<213> ORGANISM: Artificial Sequence
<220> FEATURE:
<223> OTHER INFORMATION: Description of Artificial Sequence: Synthetic
      template oligonucleotide
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (23)..(24)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g

<400> SEQUENCE: 28
gttcctcatt ctctgaagan ngnntnnann cnngnnttnn gnncnnannt nnannacttc    60
agctgccccg g                                                        71

<210> SEQ ID NO 29
<211> LENGTH: 71
<212> TYPE: DNA
<213> ORGANISM: Artificial Sequence
<220> FEATURE:
<223> OTHER INFORMATION: Description of Artificial Sequence: Synthetic
      template oligonucleotide
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (23)..(24)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g

<400> SEQUENCE: 29
gttcctcatt ctctgaagan ntnnanncnn gnntnnaann tnngnncnna nnannacttc    60
agctgccccg g                                                        71

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      RCA primer

```
<400> SEQUENCE: 30
aatgaggaac ccggggcagc                                               20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      sequencing primer

<400> SEQUENCE: 31
acttcagctg ccccgggt                                                 18

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide probe
<220> FEATURE:
<223> OTHER INFORMATION: Description of Combined DNA/RNA Molecule:
      Synthetic oligonucleotide probe
<220> FEATURE:
<221> NAME/KEY: modified_base
<222> LOCATION: (16)..(18)
<223> OTHER INFORMATION: a, c, t or g
<220> FEATURE:
<221> NAME/KEY: modified_base
<222> LOCATION: (20)..(21)
<223> OTHER INFORMATION: a, c, t or g

<400> SEQUENCE: 32
acgctggaac agcgunnnan n                                             21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide probe
<220> FEATURE:
<223> OTHER INFORMATION: Description of Combined DNA/RNA Molecule:
      Synthetic oligonucleotide probe
<220> FEATURE:
<221> NAME/KEY: modified_base
<222> LOCATION: (16)..(18)
<223> OTHER INFORMATION: a, c, t or g
<220> FEATURE:
<221> NAME/KEY: modified_base
<222> LOCATION: (20)..(21)
<223> OTHER INFORMATION: a, c, t or g

<400> SEQUENCE: 33
acgctggaac agcgunnncn n                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide probe
<220> FEATURE:
<223> OTHER INFORMATION: Description of Combined DNA/RNA Molecule:
      Synthetic oligonucleotide probe
```

```
<220> FEATURE:
<221> NAME/KEY: modified_base
<222> LOCATION: (16)..(18)
<223> OTHER INFORMATION: a, c, t or g
<220> FEATURE:
<221> NAME/KEY: modified_base
<222> LOCATION: (20)..(21)
<223> OTHER INFORMATION: a, c, t or g

<400> SEQUENCE: 34
acgctggaac agcgunnngn n                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide probe
<220> FEATURE:
<223> OTHER INFORMATION: Description of Combined DNA/RNA Molecule:
      Synthetic oligonucleotide probe
<220> FEATURE:
<221> NAME/KEY: modified_base
<222> LOCATION: (16)..(18)
<223> OTHER INFORMATION: a, c, t or g
<220> FEATURE:
<221> NAME/KEY: modified_base
<222> LOCATION: (20)..(21)
<223> OTHER INFORMATION: a, c, t or g

<400> SEQUENCE: 35
acgctggaac agcgunnntn n                                              21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe CY5 detectable moiety
<220> FEATURE:
<223> OTHER INFORMATION: Description of Combined DNA/RNA Molecule:
      Synthetic oligonucleotide probe CY5 detectable moiety
<220> FEATURE:
<221> NAME/KEY: modified_base
<222> LOCATION: (1)..(5)
<223> OTHER INFORMATION: a, c, t or g

<400> SEQUENCE: 36
nnnnnaucgt catgccaaac ga                                             22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe TR detectable moiety
<220> FEATURE:
<223> OTHER INFORMATION: Description of Combined DNA/RNA Molecule:
      Synthetic oligonucleotide probe TR detectable moiety
<220> FEATURE:
<221> NAME/KEY: modified_base
<222> LOCATION: (1)..(5)
<223> OTHER INFORMATION: a, c, t or g

<400> SEQUENCE: 37
nnnnncucgt catgccaaac ga                                             22
```

```
<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe FITC detectable moiety
<220> FEATURE:
<223> OTHER INFORMATION: Description of Combined DNA/RNA Molecule:
      Synthetic oligonucleotide probe FITC detectable moiety
<220> FEATURE:
<221> NAME/KEY: modified_base
<222> LOCATION: (1)..(5)
<223> OTHER INFORMATION: a, c, t or g

<400> SEQUENCE: 38
nnnnntucgt catgccaaac ga                                              22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe CY3 detectable moiety
<220> FEATURE:
<223> OTHER INFORMATION: Description of Combined DNA/RNA Molecule:
      Synthetic oligonucleotide probe CY3 detectable moiety
<220> FEATURE:
<221> NAME/KEY: modified_base
<222> LOCATION: (1)..(5)
<223> OTHER INFORMATION: a, c, t or g

<400> SEQUENCE: 39
nnnnngucgt catgccaaac ga                                              22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe CY5 detectable moiety
<220> FEATURE:
<223> OTHER INFORMATION: Description of Combined DNA/RNA Molecule:
      Synthetic oligonucleotide probe CY5 detectable moiety
<220> FEATURE:
<221> NAME/KEY: modified_base
<222> LOCATION: (1)..(5)
<223> OTHER INFORMATION: a, c, t or g

<400> SEQUENCE: 40
nnnnncucgt gatatcagac ga                                              22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe TR detectable moiety
<220> FEATURE:
<223> OTHER INFORMATION: Description of Combined DNA/RNA Molecule:
      Synthetic oligonucleotide probe TR detectable moiety
<220> FEATURE:
<221> NAME/KEY: modified_base
<222> LOCATION: (1)..(5)
<223> OTHER INFORMATION: a, c, t or g

<400> SEQUENCE: 41
nnnnntucgt ccaccaaaac ga                                              22
```

```
<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide probe CY3 detectable moiety
<220> FEATURE:
<223> OTHER INFORMATION: Description of Combined DNA/RNA Molecule:
      Synthetic oligonucleotide probe CY3 detectable moiety
<220> FEATURE:
<221> NAME/KEY: modified_base
<222> LOCATION: (1)..(5)
<223> OTHER INFORMATION: a, c, t or g

<400> SEQUENCE: 42
nnnnngucgt tattagccgg ctatacga                                        28
```

SEQUENCING BY STRUCTURE ASSEMBLY

RELATED APPLICATION DATA

This application is a National Stage Application under 35 U.S.C. 371 of co-pending PCT application PCT/US2012/059873 now WO/2013/055995 designating the United States and filed Oct. 12, 2012; which claims the benefit of U.S. provisional application No. 61/609,990 and filed Mar. 13, 2012, which claims the benefit of U.S. provisional application No. 61/547,138 and filed Oct. 14, 2011 each of which are hereby incorporated by reference in their entireties.

STATEMENT OF GOVERNMENT INTERESTS

This invention was made with Government support under NIH Grant Number 5P50HG005550-02. The Government has certain rights in the invention.

This application includes as part of its subject matter a substitute Sequence Listing electronically submitted via EFS-Web on Apr. 10, 2017, as a single text file named 010498.00494_US_SL.txt". The substitute Sequence Listing text file was created on Apr. 7, 2017 and is 18,121 bytes in size.

FIELD

The present invention relates to methods of sequencing nucleic acids.

BACKGROUND

Sequencing methods are known. See for example Shendure et al., Accurate multiplex polony sequencing of an evolved bacterial genome, *Science*, vol. 309, p. 1728-32. 2005; Drmanac et al., Human genome sequencing using unchained base reads on self-assembling DNA nanoarrays, *Science*, vol. 327, p. 78-81. 2009; McKernan et al., Sequence and structural variation in a human genome uncovered by short-read, massively parallel ligation sequencing using two-base encoding, *Genome Res.*, vol. 19, p. 1527-41. 2009; Rodrigue et al., Unlocking short read sequencing for metagenomics, *PLoS One*, vol. 28, e11840. 2010; Rothberg et al., An integrated semiconductor device enabling non-optical genome sequencing, *Nature*, vol. 475, p. 348-352. 2011; Margulies et al., Genome sequencing in microfabricated high-density picolitre reactors, *Nature*, vol. 437, p. 376-380. 2005; Rasko et al. Origins of the *E. coli* strain causing an outbreak of hemolytic-uremic syndrome in Germany, *N. Engl. J. Med.*, Epub. 2011; Hutter et al., Labeled nucleoside triphosphates with reversibly terminating aminoalkoxyl groups, *Nucleos. Nucleot. Nucl.*, vol. 92, p. 879-895. 2010; Seo et al., Four-color DNA sequencing by synthesis on a chip using photocleavable fluorescent nucleotides, *Proc. Natl. Acad. Sci. USA.*, Vol. 102, P. 5926-5931 (2005); Olejnik et al.; Photocleavable biotin derivatives: a versatile approach for the isolation of biomolecules, *Proc. Natl. Acad. Sci. U.S.A.*, vol. 92, p. 7590-7594. 1995; U.S. Pat. No. 5,750,34; US 2009/0062129 and US 2009/0191553.

SUMMARY

Embodiments of the present disclosure are directed to methods for determining the sequence of nucleotides in a target polynucleotide using sequencing by ligation and/or sequencing by hybridization. Certain aspects include repeated cycles of duplex extension along a nucleic acid template, such as a single stranded nucleic acid template, using probes that facilitate detection of one or more or all of the nucleotides in an oligonucleotide probe that is hybridized and/or ligated in duplex extension to the nucleic acid template. According to one aspect, multiple nucleotides in an oligonucleotide probe, and their complementary nucleotides in a nucleic acid template, can be identified as a result of a single ligation cycle. Certain oligonucleotide probes of the present disclosure include a template non-hybridizing nucleic acid sequence. That is, the template non-hybridizing nucleic acid sequence does not hybridize to the template nucleic acid sequence. The template non-hybridizing nucleic acid may include a detectable moiety corresponding to a known nucleotide in the oligonucleotide probe. The detectable moiety is detected. The template non-hybridizing nucleic acid may include a probe hybridization site corresponding to a known nucleotide in the oligonucleotide probe. A probe with a detectable moiety is then hybridized to the probe hybridization site and the detectable moiety is detected. According to certain aspects, a nucleotide in the oligonucleotide probe is identified by detecting a corresponding detectable moiety and, accordingly, a complementary nucleotide in the template nucleic acid is identified.

According to still certain aspects, the template non-hybridizing nucleic acid may be detached from the oligonucleotide probe and an additional oligonucleotide probe having a template non-hybridizing nucleic acid may then be ligated and a nucleotide in the oligonucleotide probe identified by detecting a detectable moiety. According to further aspects, an oligonucleotide probe may include a template nonhybridizing nucleic acid flanked on either side by an oligonucleotide probe suitable for hybridization and ligation.

According to the present disclosure, cycles of ligation and detection may be carried out along the length of the template nucleic acid in either the 5' to 3' direction or the 3' to 5' direction. Then, the process may be repeated starting again from either the 5' or 3' direction to identify additional nucleotides in the template nucleic acid. The process may be repeated until some, a plurality or all of the nucleotides in the template nucleic acid are identified as desired. According to an additional aspect, cycles of ligation and detection may be carried out in both the 5' to 3' direction and the 3' to 5' direction in parallel. According to one aspect, nucleotides may be identified as a result of ligations at the 5' end or as a result of ligations at the 3' end or both. Certain embodiments of the present disclosure discussed herein utilize different detectable moieties capable of identifying two or more different oligonucleotides at the same time, as the different detectable moieties are capable of differentiating between different oligonucleotides. As an example, detectable moieties may have wavelengths different enough to be distinguishable. According to this aspect, as many oligonucleotides could be identified as there are distinguishable detectable moieties.

According to one aspect, a sequencing primer is hybridized to a single stranded nucleic acid template. An oligonucleotide probe is hybridized to the single stranded nucleic acid template and ligated to the sequencing primer to form an extended hybridized sequence. According to one aspect of the present disclosure, the oligonucleotide probe includes a template-nonhybridizing nucleic acid structure. One feature of the template-nonhybridizing nucleic acid structure is that it may prevent or inhibit or block multiple ligations of the oligonucleotide probe such that a single ligation occurs in a single cycle. Another feature of the template-nonhybridizing nucleic acid structure is that it facilitates perfectly matched hybridization of the oligonucleotide probe as the template-nonhybridizing nucleic acid structure includes a nucleotide directly attached to the oligonucleotide probe and where such nucleotide does not hybridize to the template nucleic acid. Accordingly, an additional feature of the template-nonhybridizing nucleic acid structure is that it may be immediately adjacent and/or attached to the terminal hybridized nucleotide in the oligonucleotide probe such that the oligonucleotide probe is hybridized to the single stranded nucleic acid template while the template-nonhybridizing nucleic acid structure is not. Such a combination of an oligonucleotide probe and template-nonhybridizing nucleic acid structure reduces bias insofar as the number of nucleotides in the oligonucleotide probe hybridized to the template nucleic acid is fixed and in some embodiments the terminal hybridized nucleotide of the oligonucleotide probe is extendable for further ligation.

The template-nonhybridizing nucleic acid structure includes one or more detectable moieties which correspond to one or more known nucleotides in the oligonucleotide probe. One such nucleotide is the terminal hybridized nucleotide in the oligonucleotide probe. According to this exemplary aspect, a set of oligonucleotide probes include an A, C, G, or T as the terminal hybridized nucleotide with a different detectable moiety corresponding to one of A, C, G, or T. Since the detectable moiety corresponds to a known nucleotide, detection of the detectable moiety confirms hybridization and/or ligation of a particular oligonucleotide probe from within the set and the identity of the terminal hybridized nucleotide of the oligonucleotide probe. This approach may be used for any nucleotide within the oligonucleotide probe and is not limited to the terminal hybridized nucleotide.

It is to be understood that according to some aspects, the template-nonhybridizing nucleic acid structure need not be adjacent and/or attached to the terminal hybridized nucleotide in the oligonucleotide probe. Exemplary embodiments include the template-nonhybridizing nucleic acid structure adjacent and/or attached to one of the nucleotides within the oligonucleotide probe such that detection of the detectable moiety confirms hybridization and/or ligation of a particular oligonucleotide probe from within the set and the identity of the hybridized nucleotide of the oligonucleotide probe to which the template-nonhybridizing nucleic acid structure is attached, as a particular detectable moiety is associated with a known particular A, C, G, or T of the hybridized nucleotide to which the template-nonhybridizing nucleic acid structure is attached.

According to a further exemplary embodiment, the template-nonhybridizing nucleic acid structure including a detectable moiety need not be adjacent and/or attached to the nucleotide it will identify. For example, the template-nonhybridizing nucleic acid structure may be adjacent and/or attached to the terminal hybridized nucleotide, but the detectable moiety is indicative of a known A, C, G or T at a known position within the hybridized and/or ligated oligonucleotide probe. According to this aspect, the oligonucleotide probe is designed with a particular detectable moiety indicative of a particular nucleotide at a particular position along the oligonucleotide probe. As an exemplary aspect, a set of oligonucleotide probes having N nucleotides is prepared including a template-nonhybridizing nucleic acid structure adjacent and/or attached to one of the N nucleotides and indicative of one of the N nucleotides at a particular position within the oligonucleotide probe. According to this aspect, a desired nucleotide anywhere within the oligonucleotide probe may be identified for a given cycle of hybridization/and or ligation and detection of the detectable moiety. According to a further aspect, an oligonucleotide probe may include a different detectable moiety for each one of the N nucleotides of the oligonucleotide probes. According this aspect, hybridization and/or ligation of the oligonucleotide probe allows detection of each of the N nucleotides in the oligonucleotide probe as a result of a single hybridization and/or ligation of an oligonucleotide probe.

The template-nonhybridizing nucleic acid structure may include one or more probe hybridization sites for hybridizing with a probe including a detectable moiety with each probe hybridization site corresponding to a nucleotide in the oligonucleotide probe. For example, the oligonucleotide probe may include a template-nonhybridizing nucleic acid structure with a probe hybridization site corresponding to the known terminal hybridized nucleotide in the oligonucleotide probe. Hybridizing a probe with a detectable moiety to the probe hybridization site on the template-nonhybridizing nucleic acid structure and detecting the detectable moiety identifies the terminal hybridized nucleotide, and the corresponding complementary nucleotide in the template nucleic acid.

The template-nonhybridizing nucleic acid structure may include a plurality of probe hybridization sites with each probe hybridization site corresponding to a particular nucleotide at a particular position in the oligonucleotide probe. According to this aspect, for an oligonucleotide of N nucleotides, the template-nonhybridizing nucleic acid structure may have N probe hybridization sites, with each probe hybridization site corresponding to a specific nucleotide at a specific location along the oligonucleotide probe. According to an additional aspect, for an oligonucleotide of N nucleotides, the template-nonhybridizing nucleic acid structure may have N or fewer probe hybridization sites, with each probe hybridization site corresponding to a specific nucleotide at a specific location along the oligonucleotide probe. According to this aspect, the oligonucleotide probe may include a template-nonhybridizing nucleic acid structure having 1, 2, 3, 4, 5, or 6, etc., or up to N probe hybridization sites such that the oligonucleotide probe can be used to detect one nucleotide, N nucleotides or fewer than N nucleotides. Embodiments of the present disclosure include the use of probes described herein for detecting and identifying a plurality of nucleotides in an oligonucleotide probe as a result of a single ligation step or cycle.

According to one aspect of the present disclosure, a template-nonhybridizing nucleic acid structure is cleavably attached to the oligonucleotide probe. The template-nonhybridizing nucleic acid structure has a cleavable nucleotide immediately attached to a terminal hybridized nucleotide of the oligonucleotide probe. According to this aspect, such a combination promotes cleavage at the desired cleavage site leaving a precise oligonucleotide probe of known length thereby reducing bias. According to an additional aspect, an optional step is provided of removing the template-nonhybridizing nucleic acid structure by cleavage of the cleavable nucleotide and generating an extendable terminus on the extended hybridized sequence. According to one aspect, the step of cleaving can generate an extendable terminus available for ligation. According to an alternate aspect, a nonextendable terminus of the oligonucleotide probe can be modified to be an extendable terminus available for ligation. According to this aspect, additional oligonucleotide probes can then repeatedly be hybridized and ligated in series along the single stranded nucleic acid template wherein after each ligation, one or more or all of the nucleotides of the hybridized and ligated oligonucleotide probe are identified and one or more or all of the complementary nucleotides in the template nucleic acid are identified.

In order to sequence each nucleotide in the template nucleic acid template, the ligation and/or hybridization methods described herein may be repeated along the length of the template nucleic acid template and then the methods repeated one or more nucleotides out of phase along the length of the template nucleic acid compared to the sequencing method previously performed. In this manner, where a single nucleotide is identified using an oligonucleotide primer of N nucleotides (as an example), ligation and/or hybridization is repeated N−1 times one nucleotide out of phase. Stated differently, the starting nucleotide in each successive sequencing method is out of phase by one nucleotide thereby allowing the identification of successive nucleotides of the template nucleic acid.

According to an additional aspect of the methods of the present disclosure, a dual probe is provided that includes a first oligonucleotide probe, a template non-hybridizing nucleic acid structure and a second oligonucleotide probe. According to one aspect, the template non-hybridizing nucleic acid structure is intermediate the first oligonucleotide probe and the second oligonucleotide probe such that the first oligonucleotide probe and the second oligonucleotide probe may hybridize to the nucleic acid template with the template non-hybridizing nucleic acid structure therebetween.

A sequencing primer is hybridized to a nucleic acid template. The first oligonucleotide probe and the second oligonucleotide probe of the dual probe each hybridize to the single stranded nucleic acid template with the first oligonucleotide probe being ligated to the sequencing primer to form an extended hybridized sequence. According to one aspect, the template-nonhybridizing nucleic acid structure includes a detectable moiety which corresponds to a nucleotide in either the first oligonucleotide probe or the second oligonucleotide probe as described above. According to an additional aspect, the template-nonhybridizing nucleic acid structure includes a probe hybridization site for hybridizing with a probe including a detectable moiety which corresponds to a nucleotide in either the first oligonucleotide probe or the second oligonucleotide probe as described above. According to certain aspects, a nucleotide in either the first oligonucleotide probe or the second oligonucleotide probe is identified by detecting a corresponding detectable moiety as described above and, accordingly, a complementary nucleotide in the single stranded nucleic acid is identified. According to one aspect, the template-nonhybridizing nucleic acid structure may include a probe hybridization site for each nucleotide in the first oligonucleotide probe or the second oligonucleotide probe or both. According to this aspect, the entire sequence of either the first oligonucleotide probe or the second oligonucleotide probe or both may be determined from a single ligation cycle. According to a further aspect, the second oligonucleotide probe includes an extendable terminus available for ligation. Alternatively, the second oligonucleotide probe can be modified to include an extendable terminus available for ligation. According to this aspect, additional dual probes can then repeatedly be hybridized and ligated in series along the single stranded nucleic acid template wherein after each ligation, a nucleotide of either the first or second oligonucleotide probe is identified and a complementary nucleotide in the single stranded nucleic acid is identified, or additionally, each of the nucleotides in either the first or second oligonucleotide probe or both may be identified with each ligation cycle.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

The principles of the present invention may be applied with particular advantage to determine the identity of oligonucleotide sequences. Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, Biochemistry, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Figure 1:
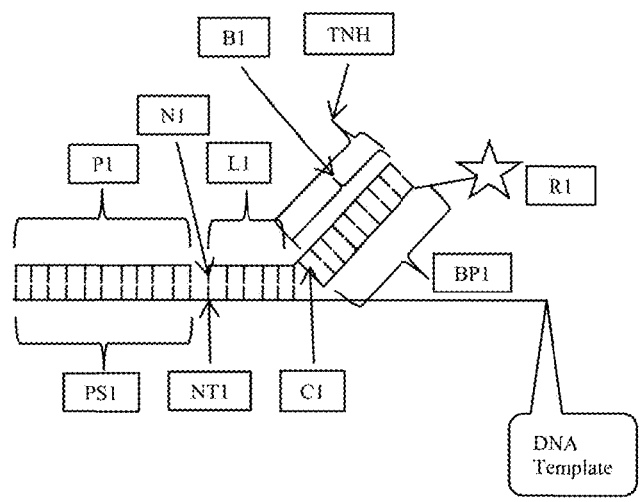
FIG. 1 is a schematic depicting hybridization of an oligonucleotide probe to a DNA template and having a template nonhybridizing nucleic acid sequence according to one aspect of the present disclosure.

FIG. 1 depicts aspects of certain embodiments of the methods and probes described herein. According to FIG. 1, a nucleic acid template is provided. The nucleic acid template may include a single stranded nucleic acid template, such as a single stranded DNA template as indicated by DNA Template in FIG. 1. As shown in FIG. 1, a sequencing primer P1 is hybridized to a sequencing primer hybridization site PS1. Adjacent to the sequencing primer hybridization site on the nucleic acid template is a first template nucleotide NT1 followed by template nucleotides NT2 to NT6. As shown in FIG. 1, oligonucleotide probe L1 is hybridized to the nucleic acid template and includes nucleotides N1 to N6 which hybridize respectively to NT1 to NT6. Nucleotide N1 is ligated to the terminal nucleotide of the sequencing primer. N6 is the most distal nucleotide from N1 and the sequencing primer P1. Connected to oligonucleotide probe L1 is a template non-hybridizing nucleic acid structure TNH. Template non-hybridizing nucleic acid structure TNH is connected to nucleotide N6 of the oligonucleotide probe L1 by a cleavable nucleotide C1. The cleavable nucleotide C1 may also be referred to as a cut site or cleaving site as the cleavable nucleotide C1 is removed from the oligonucleotide probe L1. Template non-hybridizing nucleic acid structure TNH includes a probe hybridization site B1 also referred to as a barcode site insofar as the barcode corresponds to or identifies a particular nucleotide at a particular location on the oligonucleotide probe. A barcode probe BP1 hybridizes with the barcode site or probe hybridization site B1. The barcode probe BP1 includes a detectable moiety or label or reporter R1. According to the embodiment of FIG. 1, the barcode site B1 corresponds to one of the nucleotides N1 to N6, which is known by design. In this manner, if the barcode site B1 hybridizes to a barcode probe BP1 and the detectable moiety or label or reporter R1 is detected, then the nucleotide in the oligonucleotide probe L1 is identified. Hybridization of the barcode probe B1 and detection of the detectable moiety R1 identifies the nucleotide to which the barcode corresponds, and accordingly, the complementary nucleotide to which the nucleotide is hybridized.

Figure 1A:
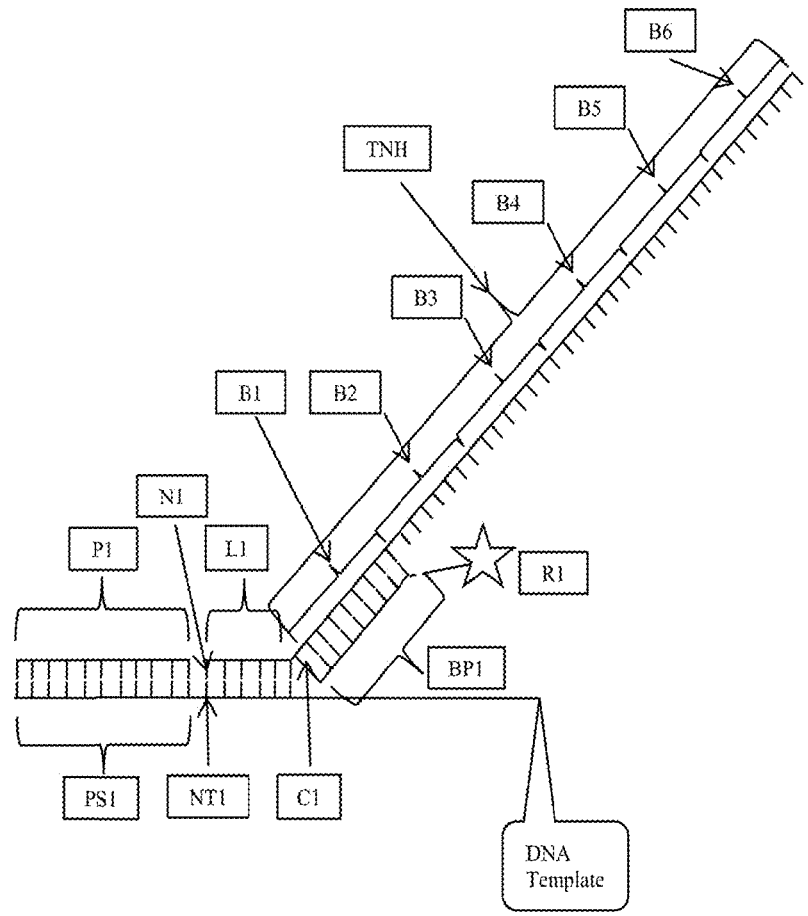
FIG. 1A is a schematic depicting hybridization of an oligonucleotide probe to a DNA template and having a template nonhybridizing nucleic acid sequence according to an alternate aspect of the present disclosure.

FIG. 1A is an exemplary embodiment of the present disclosure wherein the template non-hybridizing nucleic acid structure TNH includes probe hybridization sites B1 to B6 also referred to as barcode sites. Each of B1 to B6 corresponds to one of the nucleotides N1 to N6 which are known by design in the oligonucleotide probe L1. According to one aspect, barcode site B1 corresponds to known nucleotide N1, barcode site B2 corresponds to known nucleotide N2, barcode site B3 corresponds to known nucleotide N3, barcode site B4 corresponds to known nucleotide N4, barcode site B5 corresponds to known nucleotide N5, and barcode site B6 corresponds to known nucleotide N6. The barcode sites B1 to B6 may be placed in series along the template non-hybridizing nucleic acid structure TNH as shown in FIG. 1A or they may be randomly placed along the template non-hybridizing nucleic acid structure TNH. All that is required is that a barcode site corresponds to a specific known nucleotide at a specific known location in the oligonucleotide probe L1 such that hybridization of the barcode site with a hybridization probe and detectable label identifies the nucleotide and its location in the oligonucleotide probe when the detectable label is detected, and therefore the complementary nucleotide in the template nucleic acid is also identified.

Figure 2:
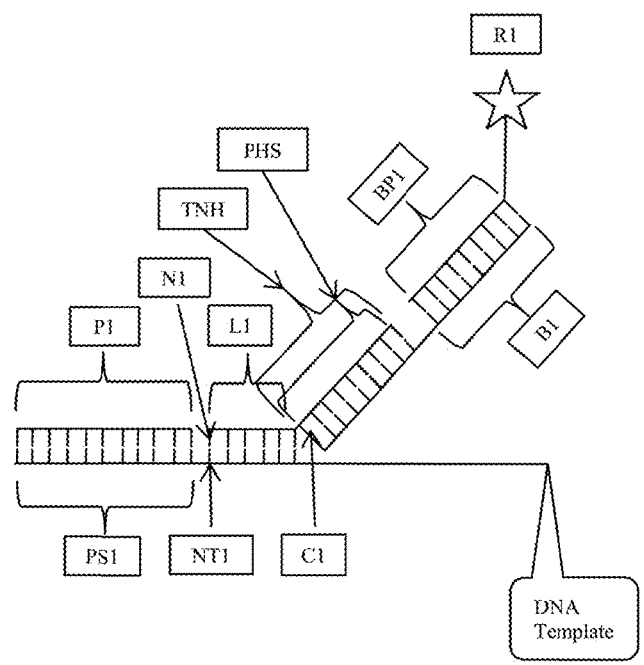
FIG. 2 is a schematic depicting hybridization of an oligonucleotide probe to a DNA template and having a template nonhybridizing nucleic acid sequence according to an alternate aspect of the present disclosure.

FIG. 2 is an exemplary embodiment of the present disclosure wherein the template non-hybridizing nucleic acid structure TNH includes a probe hybridization site PHS. Hybridized to the probe hybridization site PHS is a hybridization probe that includes a barcode site B1. As with FIG. 1, a barcode probe BP1 hybridizes with the barcode site B1. The barcode probe BP1 includes a detectable moiety or label or reporter R1. According to the embodiment of FIG. 2, the barcode site B1 corresponds to one of the nucleotides N1 to N6. Hybridization of the barcode probe B1 and detection of the detectable moiety R1 identifies the nucleotide to which the barcode corresponds.

Figure 2A:
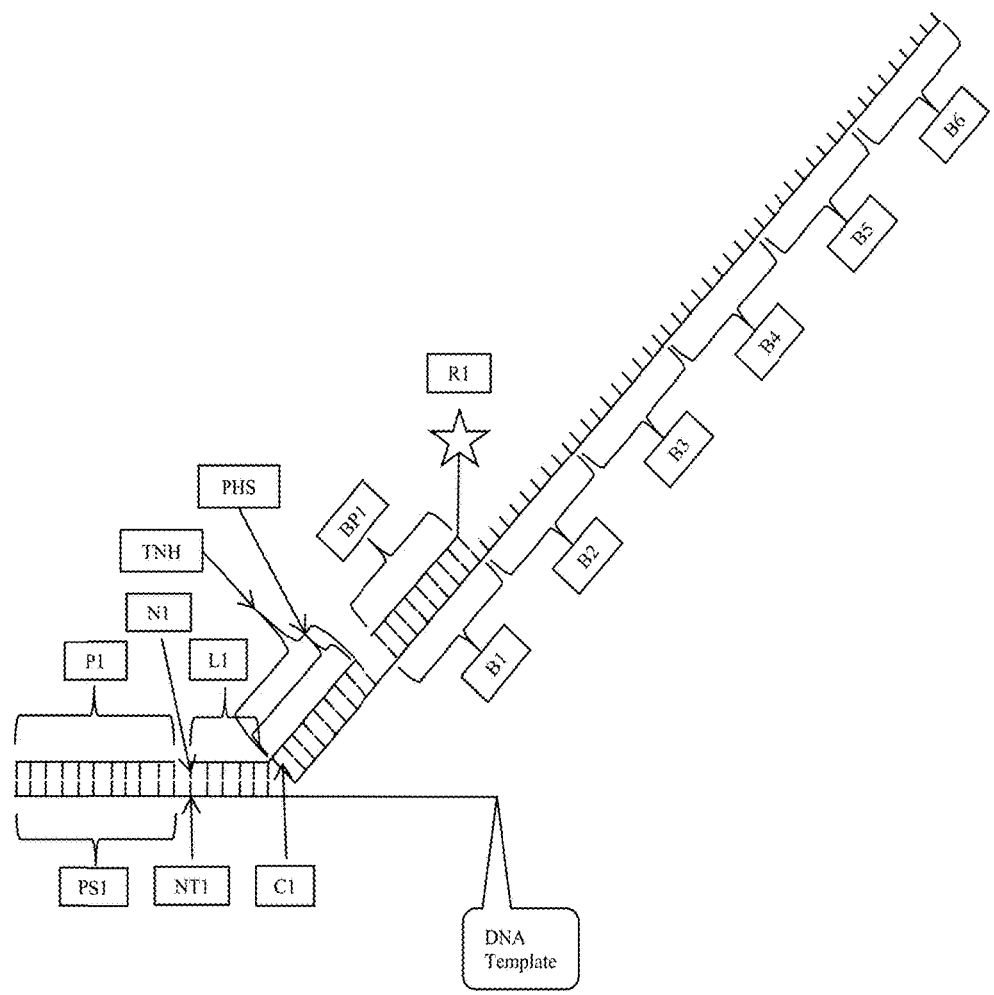
FIG. 2A is a schematic depicting hybridization of an oligonucleotide probe to a DNA template and having a template nonhybridizing nucleic acid sequence according to an alternate aspect of the present disclosure.

FIG. 2A is an exemplary embodiment of the present disclosure wherein the template non-hybridizing nucleic acid structure TNH includes a probe hybridization site PHS. Hybridized to the probe hybridization site PHS is a hybridization probe that includes a plurality of barcode sites B1 to B6. As with FIG. 1A, each of B1 to B6 corresponds to one of the nucleotides N1 to N6 in the oligonucleotide probe L1. According to one aspect, barcode site B1 corresponds to nucleotide N1, barcode site B2 corresponds to nucleotide N2, barcode site B3 corresponds to nucleotide N3, barcode site B4 corresponds to nucleotide N4, barcode site B5 corresponds to nucleotide N5, and barcode site B6 corresponds to nucleotide N6. The barcode sites B1 to B6 may be placed in series along the template non-hybridizing nucleic acid structure TNH as shown in FIG. 1B or they may be randomly placed along the template non-hybridizing nucleic acid structure TNH. All that is required is that a barcode site corresponds to a specific known nucleotide at a specific known location in the oligonucleotide probe L1 such that hybridization of the barcode site with a hybridization probe and detectable label identifies the nucleotide and its location in the oligonucleotide probe when the detectable label is detected, and therefore the complementary nucleotide in the template nucleic acid is also identified.

Figure 3:
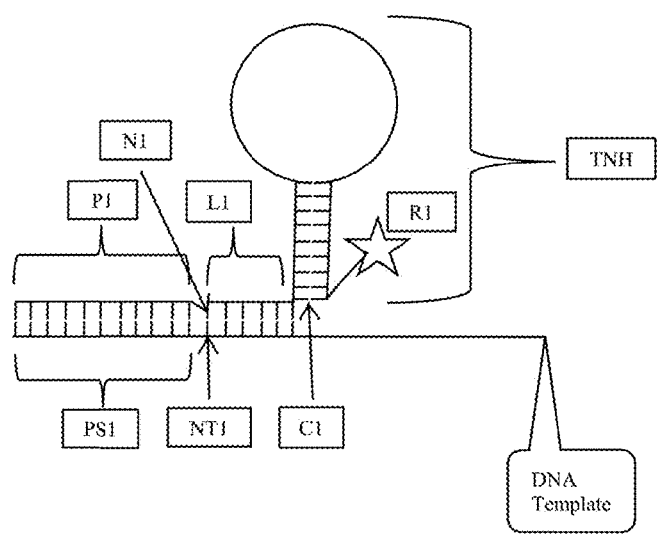
FIG. 3 is a schematic depicting hybridization of an oligonucleotide probe to a DNA template and having a template nonhybridizing nucleic acid sequence according to an alternate aspect of the present disclosure.

FIG. 3 is an exemplary embodiment of the present disclosure which includes a template non-hybridizing nucleic acid structure TNH having a hybridized portion or duplex and a nonhybridized portion. The nonhybridized portion is characterized as a stretch of one or more non-pairing nucleotides attached to the hybridized duplex forming the hybridized portion of the template non-hybridizing nucleic acid structure TNH. According to one aspect, the template non-hybridizing nucleic acid structure TNH having a hybridized portion and a nonhybridized portion may be formed by a single stranded nucleic acid where terminal portions of the single stranded nucleic acid are complementary such that they hybridize. An intermediate portion of the single stranded nucleic acid includes nonpairing nucleotides. According to this aspect, a structure referred to as a stem and loop or hairpin is provided and is shown as SL in FIG. 3. The stem portion S includes a hybridized structure and the loop portion L includes a single stranded nucleic acid with each end of the single stranded nucleic acid loop portion L connected to the stem S where nucleotides in the strand pair. It is to be understood that the stem and loop SL need only have a hybridized portion and an intermediate nonhybridized portion. Such a structure can exhibit various secondary structures such as bulges, mismatches, elbows, unpaired sections, junctions, stacks and the like known to those of skill in the art. As shown in FIG. 3, the stem of the template non-hybridizing nucleic acid structure TNH is connected to nucleotide N6 of the oligonucleotide probe L1 by a cleavable nucleotide C1. The cleavable nucleotide C1 may also be referred to as a cut site or cleaving site as the cleavable nucleotide C1 is removed from the oligonucleotide probe L1. The template non-hybridizing nucleic acid structure TNH which is in the configuration of a stem and loop SL includes a detectable moiety or label or reporter R1. The detectable moiety or label or reporter R1 may be at any position on the stem or loop SL configuration. One exemplary position is at the terminal nucleotide of the stem portion as shown in FIG. 3. The detectable moiety or label or reporter R1 corresponds to one of the nucleotides N1 to N6 of the oligonucleotide probe L1. According to one aspect, the detectable moiety or label or reporter R1 corresponds to nucleotide N6 which is the terminal hybridized nucleotide of the oligonucleotide probe L1. Accordingly, detection of the detectable moiety or label or reporter R1 identifies the corresponding nucleotide, such as N6 of the oligonucleotide probe L1. According to one aspect of the present disclosure, the stem and loop SL configuration prevents hybridization beyond the oligonucleotide probe L1. In this manner, the length of the oligonucleotide probe is exact.

Figure 4:
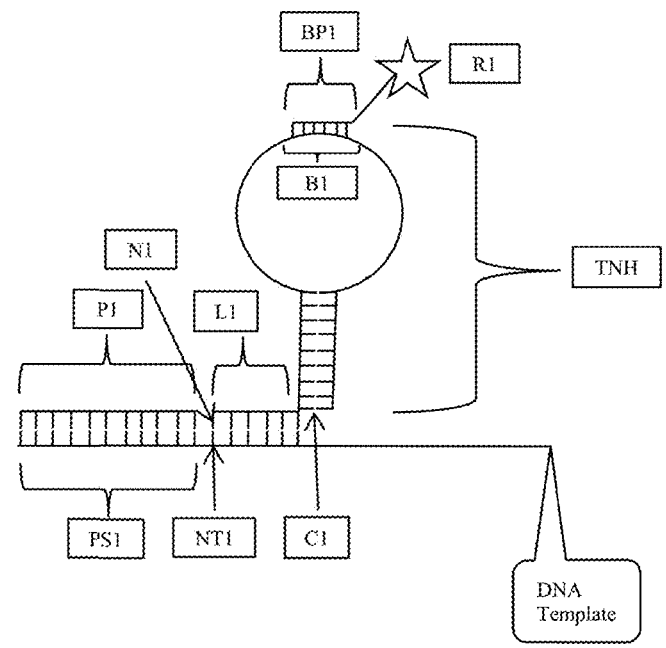
FIG. 4 is a schematic depicting hybridization of an oligonucleotide probe to a DNA template and having a template nonhybridizing nucleic acid sequence according to an alternate aspect of the present disclosure.

FIG. 4 is an exemplary embodiment of the present disclosure which includes a template non-hybridizing nucleic acid structure TNH having a hybridized portion, such as a stem, and a nonhybridized portion, such as a loop, as discussed with respect to FIG. 3. As shown in FIG. 4, the single stranded nucleic acid loop portion L includes a probe hybridization site B1 also referred to as a barcode site. A barcode probe BP1 hybridizes with the barcode site or probe hybridization site B1. The barcode probe BP1 includes a detectable moiety or label or reporter R1. According to the embodiment of FIG. 4, the barcode site B1 corresponds to one of the nucleotides N1 to N6. Hybridization of the barcode probe BP1 and detection of the detectable moiety R1 identifies the nucleotide to which the barcode corresponds.

Figure 4A:
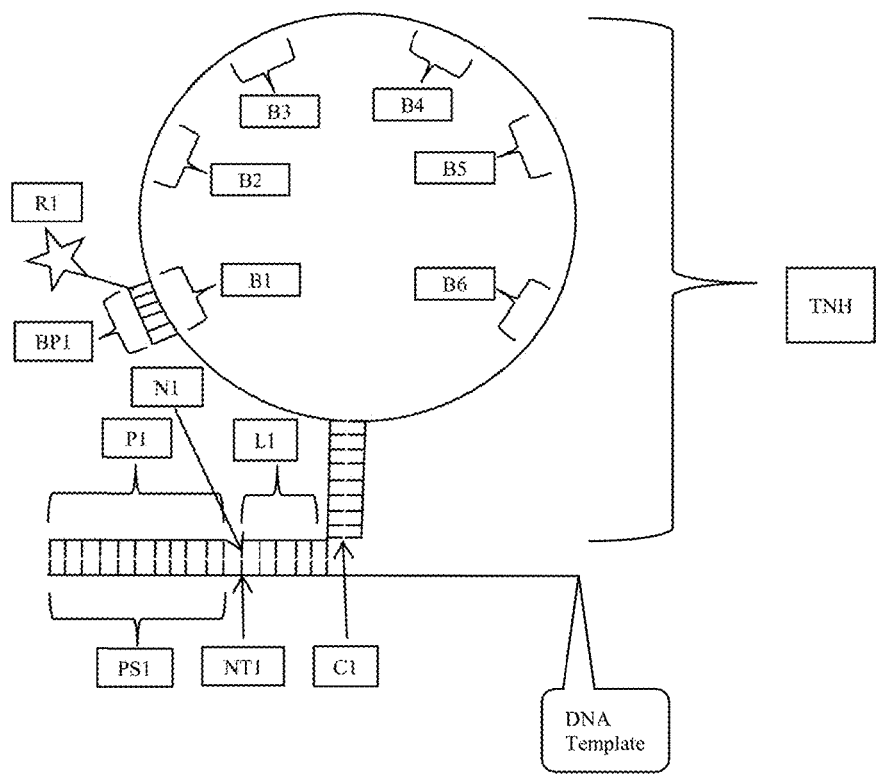
FIG. 4A is a schematic depicting hybridization of an oligonucleotide probe to a DNA template and having a template nonhybridizing nucleic acid sequence according to an alternate aspect of the present disclosure.

FIG. 4A is an exemplary embodiment of the present disclosure which includes a template non-hybridizing nucleic acid structure TNH having a hybridized portion, such as a stem, and a nonhybridized portion, such as a loop, as discussed with respect to FIG. 4. As shown in FIG. 4A, the single stranded nucleic acid loop portion L includes probe hybridization sites B1 to B6 also referred to as barcode sites. Each of B1 to B6 corresponds to one of the nucleotides N1 to N6 in the oligonucleotide probe L1. According to one aspect, barcode site B1 corresponds to nucleotide N1, barcode site B2 corresponds to nucleotide N2, barcode site B3 corresponds to nucleotide N3, barcode site B4 corresponds to nucleotide N4, barcode site B5 corresponds to nucleotide N5, and barcode site B6 corresponds to nucleotide N6. The barcode sites B1 to B6 may be placed in series along the single stranded nucleic acid loop portion L as shown in FIG. 4A or they may be randomly placed along the single stranded nucleic acid loop portion L. All that is required is that a barcode site corresponds to a specific known nucleotide at a specific known location in the oligonucleotide probe L1 such that hybridization of the barcode site with a hybridization probe and detectable label identifies the nucleotide and its location in the oligonucleotide probe when the detectable label is detected, and therefore the complementary nucleotide in the template nucleic acid is also identified.

Figure 5:
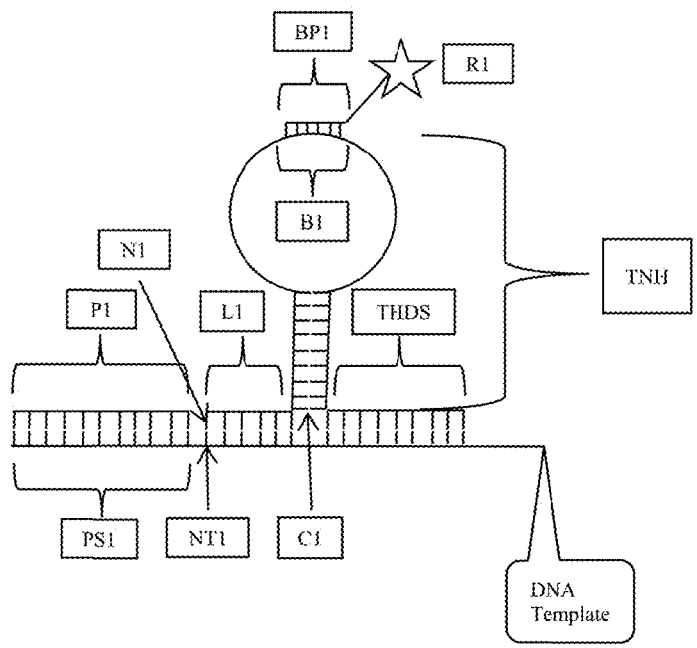
FIG. 5 is a schematic depicting hybridization of an oligonucleotide probe to a DNA template and having a template nonhybridizing nucleic acid sequence according to an alternate aspect of the present disclosure.

FIG. 5 is an exemplary embodiment of the present disclosure which includes a template non-hybridizing nucleic acid structure TNH having a hybridized portion, such as a stem, and a nonhybridized portion, such as a loop, as discussed with respect to FIG. 4. As shown in FIG. 5, a terminal hybridized distal strand THDS is attached to the stem S such that the stem and loop structure SL is intermediate the oligonucleotide probe L1 and the terminal hybridized distal strand THDS.

Figure 5A:
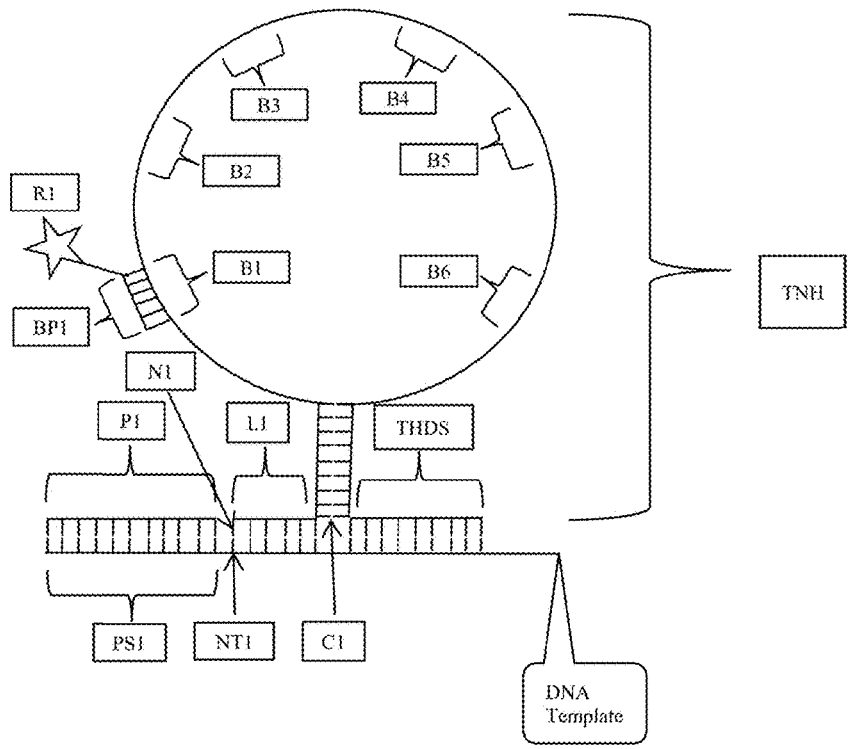
FIG. 5A is a schematic depicting hybridization of an oligonucleotide probe to a DNA template and having a template nonhybridizing nucleic acid sequence according to an alternate aspect of the present disclosure.

FIG. 5A is an exemplary embodiment of the present disclosure which includes a template non-hybridizing nucleic acid structure TNH having a hybridized portion, such as a stem, and a nonhybridized portion, such as a loop, as discussed with respect to FIG. 4A. As shown in FIG. 5A, a terminal hybridized distal strand THDS is attached to the stem S such that the stem and loop structure SL is intermediate the oligonucleotide probe L1 and the terminal hybridized distal strand THDS.

Figure 6:
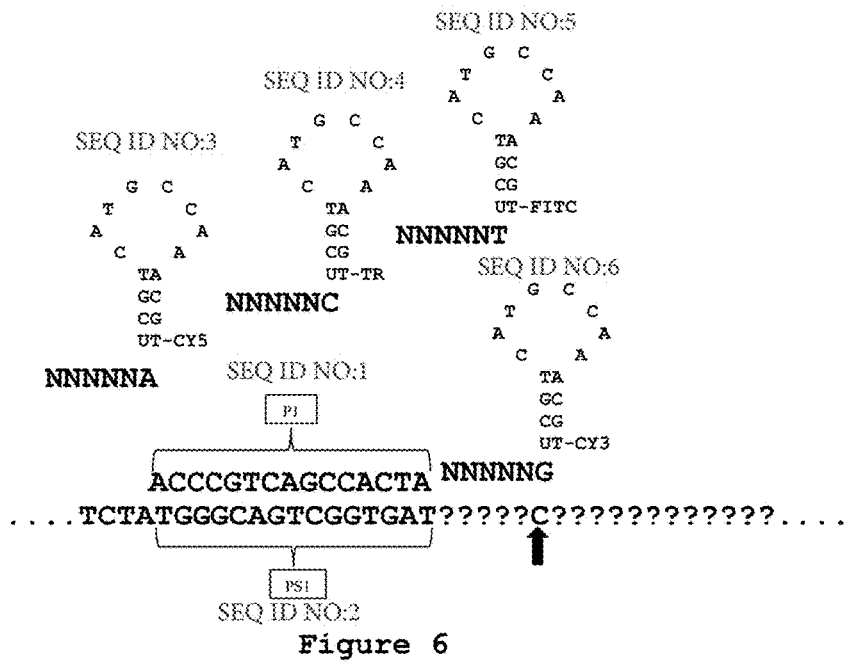
FIG. 6 is a schematic depicting use of oligonucleotide probes having template nonhybridizing nucleic acid sequences and detectable moieties to identify a nucleotide at a position in the oligonucleotide probe and its complementary nucleotide in a template DNA.

FIG. 6 is an exemplary embodiment of the present disclosure which illustrates a sequencing primer P1 hybridized to a sequencing primer hybridization site on a nucleic acid template. Oligonucleotide probes are introduced with a known nucleotide at the N6 position for hybridizing to the nucleic acid template and ligating to the sequencing primer P1. In the exemplary embodiment of FIG. 6, each oligonucleotide probe includes a template nonhybridizing nucleic acid structure in the form of a stem and loop configuration with a detectable moiety attached to the stem position at a terminal nucleotide. The detectably moiety is shown as being attached to a "U-T" base paring on the stem position. The "U-T" base pairing is attached to the oligonucleotide probe. Although particular nucleotides are shown, these are representative as a schematic only as one of skill in the art will understand how to design any particular nucleic acid sequence forming a stem and loop configuration based on the present disclosure. In each oligonucleotide probe, the nucleotide at the N6 position is known and the detectable moiety corresponds to the known nucleotide at the N6 position. As shown in FIG. 6, a different detectable moiety corresponds to each of the A, C, T, and G at position N6 of the oligonucleotide probe. In FIG. 6, CY5 corresponds to A in one probe, TR corresponds to C in a different probe, FITC corresponds to T in a different probe and CY3 corresponds to G in a different probe. An oligonucleotide probe that hybridizes and is ligated to the nucleic acid template can then be detected by the detectable moiety. For example, in FIG. 6, detecting CY3 indicates that an oligonucleotide probe having G at the N6 position has hybridized and ligated to the template nucleic acid. Accordingly, a C is identified at the NT6 position of the nucleic acid template, as it is the complement to G at the N6 position. This figure contains sequences set forth as SEQ ID NOs:1-6.

Figure 7:
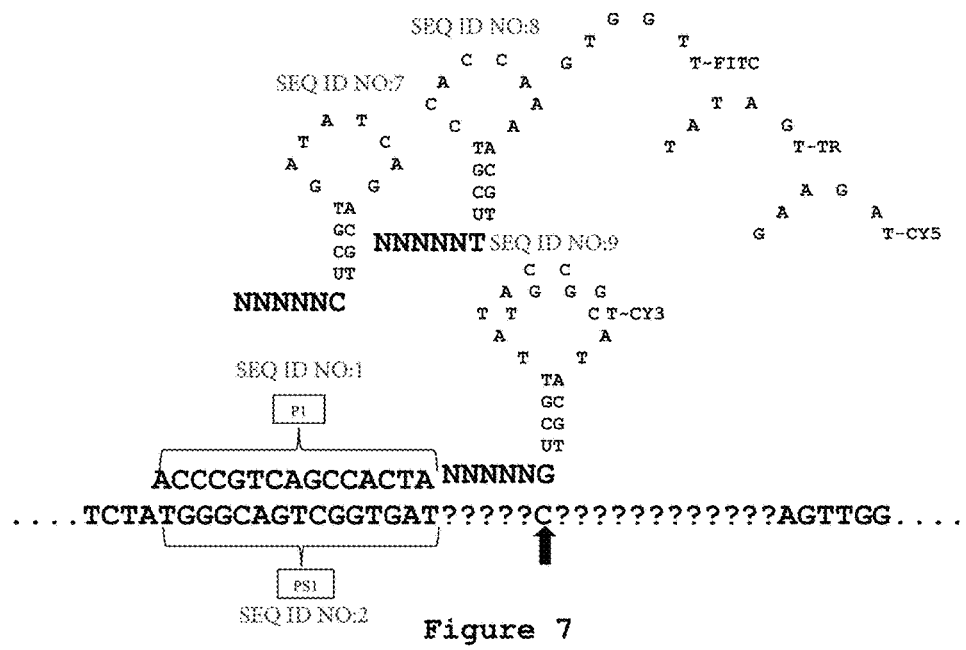
FIG. 7 is a schematic depicting use of oligonucleotide probes having template nonhybridizing nucleic acid sequences and barcode probes having detectable moieties to identify a nucleotide at a position in the oligonucleotide probe and its complementary nucleotide in a template DNA.

FIG. 7 is an exemplary embodiment of the present disclosure which illustrates a sequencing primer P1 hybridized to a sequencing primer hybridization site on a nucleic acid template. Oligonucleotide probes are introduced with a known nucleotide at the N6 position for hybridizing to the nucleic acid template and ligating to the sequencing primer P1. In the exemplary embodiment of FIG. 7, each oligonucleotide probe includes a template nonhybridizing nucleic acid structure in the form of a stem and loop configuration with the single stranded nucleic acid loop portion having a probe hybridization site or barcode site to which may hybridize a barcode probe including a detectable moiety. The stem position includes a "U-T" base pairing that is connected to the oligonucleotide probe. Although particular nucleotides are shown, these are representative as a schematic only as one of skill in the art will understand how to design any particular nucleic acid sequence forming a stem and loop configuration based on the present disclosure and including one or more probe hybridization sites or barcode sites. In each oligonucleotide probe, the nucleotide at the N6 position is known and the detectable moiety on a barcode probe corresponds to the known nucleotide at the N6 position. As shown in FIG. 7, a different detectable moiety corresponds to each of the A, C, T, and G at position N6 of the oligonucleotide probe. In FIG. 7, CY5 on a barcode probe corresponds to A in one probe, TR on a barcode probe corresponds to C in a different probe, FITC on a barcode probe corresponds to T in a different probe and CY3 on a barcode probe corresponds to G in a different probe. An oligonucleotide probe that hybridizes and is ligated to the nucleic acid template can then be detected by the detectable moiety on the barcode probe that hybridizes to the probe hybridization site or barcode site. For example, in FIG. 7, detecting CY3 indicates that an oligonucleotide probe having G at the N6 position has hybridized and ligated to the template nucleic acid. Accordingly, a C is identified at the NT6 position of the nucleic acid template, as it is the complement to G at the N6 position. This figure contains sequences set forth as SEQ ID NOs:1, 2 and 4-6.

Figure 10:
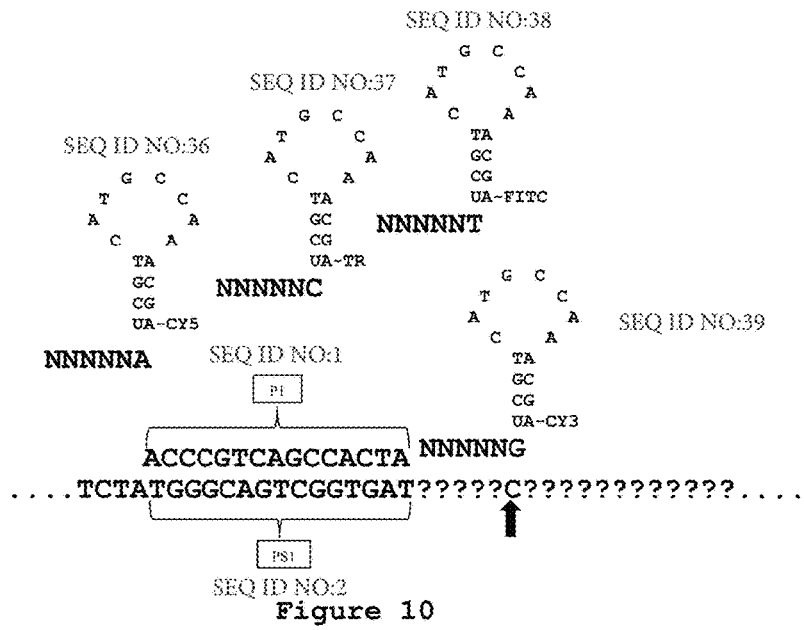
FIG. 10 is a schematic depicting use of oligonucleotide probes having template nonhybridizing nucleic acid sequences and detectable moieties to identify a nucleotide at a position in the oligonucleotide probe and its complementary nucleotide in a template DNA.

FIG. 10 is an exemplary embodiment of the present disclosure which illustrates a sequencing primer P1 hybridized to a sequencing primer hybridization site on a nucleic acid template. Oligonucleotide probes are introduced with a known nucleotide at the N6 position for hybridizing to the nucleic acid template and ligating to the sequencing primer P1. In the exemplary embodiment of FIG. 10, each oligonucleotide probe includes a template nonhybridizing nucleic acid structure in the form of a stem and loop configuration with a detectable moiety attached to the stem position at a terminal nucleotide. The detectably moiety is shown as being attached to a "U-A" base paring on the stem position. The "U-A" base pairing is attached to the oligonucleotide probe. Although particular nucleotides are shown, these are representative as a schematic only as one of skill in the art will understand how to design any particular nucleic acid sequence forming a stem and loop configuration based on the present disclosure. In each oligonucleotide probe, the nucleotide at the N6 position is known and the detectable moiety corresponds to the known nucleotide at the N6 position. As shown in FIG. 10, a different detectable moiety corresponds to each of the A, C, T, and G at position N6 of the oligonucleotide probe. In FIG. 10, CY5 corresponds to A in one probe, TR corresponds to C in a different probe, FITC corresponds to T in a different probe and CY3 corresponds to G in a different probe. An oligonucleotide probe that hybridizes and is ligated to the nucleic acid template can then be detected by the detectable moiety. For example, in FIG. 10, detecting CY3 indicates that an oligonucleotide probe having G at the N6 position has hybridized and ligated to the template nucleic acid. Accordingly, a C is identified at the NT6 position of the nucleic acid template, as it is the complement to G at the N6 position. This figure contains sequences set forth as SEQ ID NOs:1-6.

Figure 11:
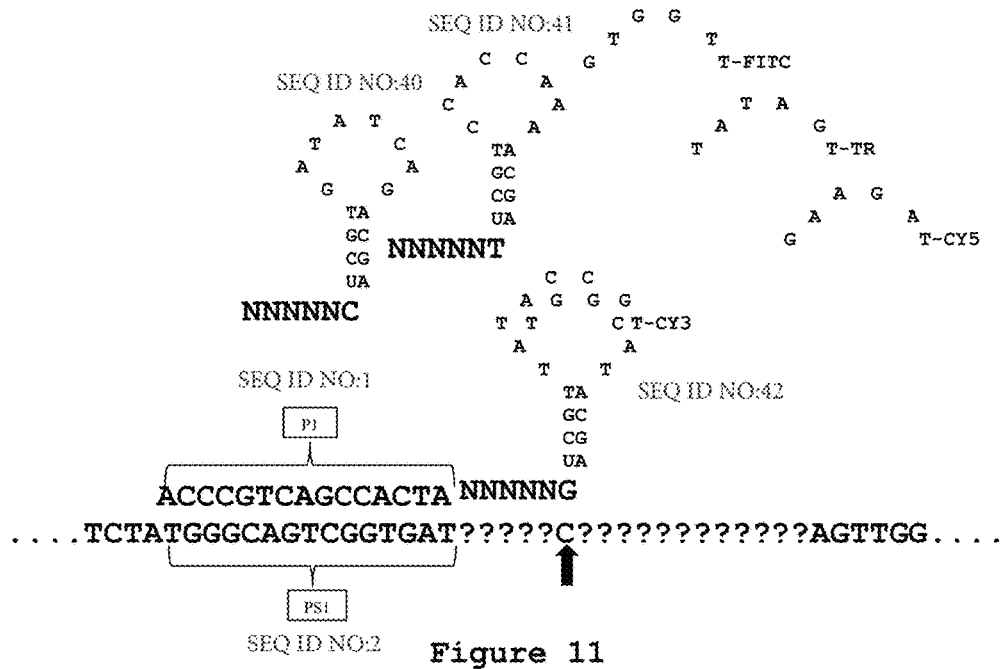
FIG. 11 is a schematic depicting use of oligonucleotide probes having template nonhybridizing nucleic acid sequences and barcode probes having detectable moieties to identify a nucleotide at a position in the oligonucleotide probe and its complementary nucleotide in a template DNA.

FIG. 11 is an exemplary embodiment of the present disclosure which illustrates a sequencing primer P1 hybridized to a sequencing primer hybridization site on a nucleic acid template. Oligonucleotide probes are introduced with a known nucleotide at the N6 position for hybridizing to the nucleic acid template and ligating to the sequencing primer P1. In the exemplary embodiment of FIG. 11, each oligonucleotide probe includes a template nonhybridizing nucleic acid structure in the form of a stem and loop configuration with the single stranded nucleic acid loop portion having a probe hybridization site or barcode site to which may hybridize a barcode probe including a detectable moiety. The stem position includes a "U-A" base pairing that is connected to the oligonucleotide probe. Although particular nucleotides are shown, these are representative as a schematic only as one of skill in the art will understand how to design any particular nucleic acid sequence forming a stem and loop configuration based on the present disclosure and including one or more probe hybridization sites or barcode sites. In each oligonucleotide probe, the nucleotide at the N6 position is known and the detectable moiety on a barcode probe corresponds to the known nucleotide at the N6 position. As shown in FIG. 11, a different detectable moiety corresponds to each of the A, C, T, and G at position N6 of the oligonucleotide probe. In FIG. 11, CY5 on a barcode probe corresponds to A in one probe, TR on a barcode probe corresponds to C in a different probe, FITC on a barcode probe corresponds to T in a different probe and CY3 on a barcode probe corresponds to G in a different probe. An oligonucleotide probe that hybridizes and is ligated to the nucleic acid template can then be detected by the detectable moiety on the barcode probe that hybridizes to the probe hybridization site or barcode site. For example, in FIG. 11, detecting CY3 indicates that an oligonucleotide probe having G at the N6 position has hybridized and ligated to the template nucleic acid. Accordingly, a C is identified at the NT6 position of the nucleic acid template, as it is the complement to G at the N6 position.

Target Polynucleotides

Target polynucleotides, also referred to as oligonucleotides or template oligonucleotides, to be sequenced according to the methods described herein can be prepared in a variety of ways known to those of skill in the art. According to one aspect, target polynucleotides are single stranded nucleic acids. The length of the target polynucleotide can vary. According to certain aspects, the length of the target polynucleotide can be between about 1 nucleotide to about 250,000 nucleotides in length. Exemplary target polynucleotide can be between about 1 nucleotide to about 100,000 nucleotides in length, between about 1 nucleotide to about 10,000 nucleotides in length, between about 1 nucleotide to about 5,000 nucleotides in length, between about 4 nucleotides to about 2,000 nucleotides in length, between about 6 nucleotides to about 2,000 nucleotides in length, between about 10 nucleotides to about 1,000 nucleotides in length, between about 20 nucleotides to about 100 nucleotides in length, and any range or value in between whether overlapping or not.

A template for sequencing can be prepared from several linear or circular sources of polynucleotides, such as dsDNA, ssDNA, cDNA, RNA and synthesized or naturally occurring oligonucleotides.

An exemplary template is a synthesized oligonucleotide of the form 5'-PO$_4$-GTT CCT CAT TCT CTG AAG ANN NNN NNN NNN NNN NNN NNN NNN NNN NNN NNN NNN NAC TTC AGC TGC CCC GG-3'-OH, (SEQ ID NO:10) where the N portion represents a ssDNA template to be identified, GTT CCT CAT TCT CTG AAG A (SEQ ID NO:11) and AC TTC AGC TGC CCC GG (SEQ ID NO:12) represent adapters that will be used as a sequencing primer hybridization site (PS1). According to aspects of the present disclosure, sequencing can be accomplished in either the 5' to 3' direction or the 3' to 5' direction or both directions simultaneously. According to certain aspects, multiple copies of the template nucleic acid are prepared using methods known to those of skill in the art. According to one aspect, the ssDNA template can be circularized using ssDNA Circligase II (Epicentre #CL9025K) or other ssDNA ligase such as Circligase I (Epicentre #CL4115K), or by template-directed ligation using a combination of a dsDNA ligase (e.g. (T3, T4, T7 and other ds DNA ligases) with a bridge oligo (5'-ATGAGGAACCCGGGGCAG-3'-PO$_4$) (SEQ ID NO:13). Chemical ligation methods have also been described (Dolinnaya et al., 1993; Kumar et al., 2007).

According to one aspect, 10 pmol of ssDNA template is circularized using Circligase II, according to the manufacturer's recommendation. Following the circularization, 20 units of Exonuclease I (Enzymatics #X801L) and 100 units of Exonuclease III (Enzymatics #X802L) are added to the reaction to digest any remaining linear template. Next, rolling circle amplification (RCA) is performed on the circular ssDNA template using a DNA polymerase with high processivity, strong displacement activity and low error rate. Rolling circle amplification methods are known to those of skill in the art and include Drmanac et al., Human genome sequencing using unchained base reads on self-assembling DNA nanoarrays, *Science*, vol. 327, p. 78-81 (2009). According to one aspect, 1 pmol of the circularized template is used with 20 units of phi29 DNA polymerase (Enzymatics #P702L). Additionally, dNTP (typically 1 mM) and a RCA primer (typically 1 pmol) are required. An exemplary RCA primer would have the form 5'-AATGAGGAACCCGGGGCA*G*C (SEQ ID NO:14), where the * represents a phosphorothioate bond thereby indicating that the last 3' nucleotide bears a phosphorotioate bond, making the RCA less susceptible to phi29 3'->5' exonuclease activity. However, an exemplary RCA primer may not include such phosphorothioate bonds, especially if the polymerase used does not have 3'->5' exonuclease activity. Alternatively, an exemplary RCA primer may have phosphorothioate bonds on the 5' side of the RCA primer such as 5'-A*A*TGAGGAACCCGGGGCAGC (SEQ ID NO:15). An annealing reaction is often performed before adding the phi29 (95° C. for 1 min, then 2 min cool down to 4° C.), to increase the RCA efficiency. Then the reaction is incubated at 30° C. for an hour (incubation periods between 15 min to 6 hours may also be used). Other temperatures can be used, since phi29 is active between 4° C. and 40° C. (with 90% diminished activity). Then, the reaction is cooled to 4° C. and the RCA products (referred to as Rolony) are recovered in cold PBS and can be stored at 4° C. until needed. Rolling circle amplification products prepared this way are stable for several months and can be used as template for assaying sequencing techniques.

A template can also be prepared using dsDNA from a biological source. The genomic DNA would first be extracted using one of the several extraction kits commercially available for that purpose. Then, the dsDNA would be fragmented to any length or a specific length, using a mechanical (Covaris focused electroacoustic, Nebulizer, sonication, vortex,) or enzymatic (e.g. Fragmentase) fragmentation. While, it is practical to keep the fragments size between 100 and 1000 nucleotides, any size can be used. The ends of the fragmented dsDNA are repaired and phosphorylated in one step using a mix of T4 DNA polymerase and T4 Polynucleotide Kinase (Enzymatics #Y914-HC-L), according to the manufacturer instructions. Other DNA polymerase with 3'->5' exonuclease activity and low or no strand displacement activity can be used. Adapters composed of dsDNA oligonucleotides are added to the dsDNA using a DNA ligase, typically T3 (Enzymatics #L601L) or T4 DNA ligase (Enzymatics #L603-HC-L). The reaction is performed at room temperature for 20 min according to the manufacturer instructions. The adapters can be in the form Ad1 5'-GTTCCTCATTCTCTGAAGA (SEQ ID NO:16), Ad2 5'-TCTTCAGAGAATGAG (SEQ ID NO:17), Ad3 5'-CCGGGGCAGCTGAAGT (SEQ ID NO:18), and Ad4 5'-ACTTCAGCTGCC (SEQ ID NO:19), where Ad1-Ad2 are annealed together and Ad3-Ad4 anneal together, before being ligated. After ligation, the 5' overhang ends are filled-in using a DNA polymerase with, such as Bst DNA polymerase large fragment (NEB #M0275L). Next, limited PCR (typically 6 to 8 cycles) is performed to generate multiple copies using PCR primer in the form 5'-PO$_4$-GTTCCTCATTCTCTGAAGA (SEQ ID NO:20) and 5'-Biotin-CCGGGGCAGCTGAAGT (SEQ ID NO:21). The 5'biotin is then attached to one end of the dsDNA to streptavidin coated magnetic beads (Invitrogen #65305), allowing the other end to be recovered by performing the Circligase II reaction, as described above, with the exception that the template is attached to the beads. This is performed by incubating the reaction at 65° C. for 2 h, which will allow the DNA strand with 5'-PO$_4$ to be de-anneal and be circularized. After exonuclease digest, the circular ssDNA template is now ready for rolling circle amplification (RCA) as discussed above. Adapters can also be in the form Ad5 5'-GAAGTCTTCTTACTCCTTGGGCCCCGTCA-GACTTC (SEQ ID NO:22) and Ad6 5'-GTTCCGA-GATTTCCTCCGTTGTTGTTAATCGGAAC (SEQ ID NO:23), where Ad5 and Ad6 each form hairpin structures to be ligated on each side of the dsDNA, virtually creating a circular ssDNA product ready for RCA. A pull down assay can be used to select templates bearing one of each hairpin and not two of the same. In this case, an oligonucleotide complementary to one loop in the form 5'-Biotin-TAACAACAACGGAGGAAA-C3sp (SEQ ID NO:24) will be bound to streptavidin coated magnetic beads. Next RCA can be performed using a RCA primer (5'-ACGGGGCCCAAGGAGTA*A*G) (SEQ ID NO:25), as described above.

Other amplification methods can be used. In general, "amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

Varied choices of polymerases exist with different properties, such as temperature, strand displacement, and proofreading. Amplification can be isothermal, as described above and in similar adaptation such as multiple displacement amplification (MDA) described by Dean et al., Comprehensive human genome amplification using multiple displacement amplification, *Proc. Natl. Acad. Sci. U.S.A.*, vol. 99, p. 5261-5266. 2002; also Dean et al., Rapid amplification of plasmid and phage DNA using phi29 DNA polymerase and multiply-primed rolling circle amplification, *Genome Res.*, vol. 11, p. 1095-1099. 2001; also Aviel-Ronen et al., Large fragment Bst DNA polymerase for whole genome amplification of DNA formalin-fixed paraffin-embedded tissues, *BMC Genomics*, vol. 7, p. 312. 2006. Amplification can also cycle through different temperature regiments, such as the traditional polymerase chain reaction (PCR) popularized by Mullis et al., Specific enzymatic amplification of DNA in vitro: The polymerase chain reaction. *Cold Spring Harbor Symp. Quant. Biol.*, vole 51, p. 263-273. 1986. Variations more applicable to genome amplification are described by Zhang et al., Whole genome amplification from a single cell: implications for genetic analysis, *Proc. Natl. Acad. Sci. U.S.A.*, vol. 89, p. 5847-5851. 1992; and Telenius et al., Degenerate oligonucleotide-primed PCR: general amplification of target DNA by a single degenerate primer, Genomics, vol. 13, p. 718-725. 1992. Other methods include Polony PCR described by Mitra and Church, In situ localized amplification and contact replication of many individual DNA molecules, *Nuc. Acid. Res.*, vole 27, pages e34. 1999; emulsion PCR (ePCR) described by Shendure et al., Accurate multiplex polony sequencing of an evolved bacterial genome, *Science*, vol. 309, p. 1728-32. 2005; and Williams et al., Amplification of complex gene libraries by emulsion PCR, *Nat. Methods*, vol. 3, p. 545-550. 2006. Any amplification method can be combined with a reverse transcription step, a priori, to allow amplification of RNA. According to certain aspects, amplification is not absolutely required since probes, reporters and detection systems with sufficient sensitivity can be used to allow detection of a single molecule using template non-hybridizing nucleic acid structures described. Ways to adapt sensitivity in a system include choices of excitation sources (e.g. illumination) and detection (e.g. photodetector, photomultipliers). Ways to adapt signal level include probes allowing stacking of reporters, and high intensity reporters (e.g. quantum dots) can also be used.

Amplification methods useful in the present disclosure may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach and PCR 2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 68-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 µL. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

In general, target polynucleotides, template nucleotides, template non-hybridizing nucleic acids or probes described herein include the terms "nucleic acid molecule," "nucleic acid sequence," "nucleic acid fragment," "oligonucleotide" and "polynucleotide" and are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Oligonucleotides useful in the methods described herein may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Oligonucleotide sequences may be isolated from natural sources or purchased from commercial sources. In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos.

6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

Solid Phase Supports

In certain exemplary embodiments, one or more template nucleic acid sequences, i.e. oligonucleotide sequences, described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. When using a support that is substantially planar, the support may be physically separated into regions, for example, with trenches, grooves, wells, or chemical barriers (e.g., hydrophobic coatings, etc.).

In certain exemplary embodiments, a support is a microarray. As used herein, the term "microarray" refers in one embodiment to a type of assay that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more of the cleavable linkers described herein. The density of non-overlapping regions containing nucleic acids in a microarray is typically greater than 100 per $cm^2$, and more typically, greater than 1000 per $cm^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics* Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994.

Sequencing Primers

Sequencing primers according to the present disclosure are those that are capable of binding to a known binding region of the target polynucleotide and facilitating ligation of an oligonucleotide probe of the present disclosure. Sequencing primers may be designed with the aid of a computer program such as, for example, DNAWorks, or Gene2Oligo. The binding region can vary in length but it should be long enough to hybridize the sequencing primer. Target polynucleotides may have multiple different binding regions thereby allowing different sections of the target polynucleotide to be sequenced. Sequencing primers are selected to form highly stable duplexes so that they remain hybridized during successive cycles of ligation. Sequencing primers can be selected such that ligation can proceed in either the 5' to 3' direction or the 3' to 5' direction or both. Sequencing primers may contain modified nucleotides or bonds to enhance their hybridization efficiency, or improve their stability, or prevent extension from a one terminus or the other.

According to one aspect, single stranded DNA templates (ssDNA) are prepared by RCA as described above to be used with sequencing primers. Alternatively single stranded template is attached to beads or nanoparticles in an emulsion and amplified through ePCR. The result is clonal beads with a single amplified ssDNA template.

For the purpose of identifying several template nucleotide sequences in parallel, the templates are diluted in PBS buffer pH 7.4, and either bound to a patterned or non-patterned substrate utilizing various attachment methods, such as Biotin-Strepavidin, azide-alkyle (e.g. click chemistry), NHS-ester or Silanization (e.g. aldehyde-, epoxy-, aminosilane). According to one aspect, rolonies are attached to a patterned surface, such as a $SiO_2$ solid surface, treated with 1% aminosilane (v/v) and let to interact for a period of time (typically between 5 minutes to 2 hours). Any unbound templates are then washed away using Wash 1 buffer.

Next, a sequencing primer (P1) is prepared and hybridized to the sequencing primer hybridizing site PS1. According to certain aspects, sequencing primers can be prepared which can hybridize to a known sequence of the template. Alternatively, during template preparation, adapters with a known nucleic acid sequence are added to the unknown nucleic acid sequence by way of ligation, amplification, transposition or recombination according to methods known to those of skill in the art and described herein. Still alternatively, sequencing primers having a certain level of degeneracy could be used to hybridize to certain positions along the template. According to one aspect, primer degeneracy is used to allow primers to hybridize semi-randomly along the template. Primer degeneracy is selected based on statistical methods known to those of skill in the art to facilitate primers hybridizing at certain intervals along the length of the template. According to this aspect, primers can be designed having a certain degeneracy which facilitates binding every N bases, such as every 100 bases, every 200 bases, every 2000 bases, every 100,000 bases. The binding of the primers along the length of the template is based on the design of the primers and the statistical likelihood that a primer design will bind about every N bases along the length of the template. Since the sequencing primer P1 will be extended by ligation, the terminal group of the sequencing primer P1 is typically synthesized to be ready to be covalently joined to the oligonucleotide probe (L1) by the DNA ligase. If the ligation occurs between the 5'end of the sequencing primer P1 and the 3'end of the oligonucleotide probe L1, a phosphate group (5'-$PO_4$) must be present on the sequencing primer P1 while a hydroxyl group (3'-OH) on the oligonucleotide probe L1, and vice-versa. To hybridize the sequencing primer P1 to the sequencing primer hybridizing site PS1, 1 uM of the sequencing primer P1 diluted in 5×SSPE buffer is used. The mixture is then incubated for a few minutes above room temperature to encourage proper annealing (typically between 1 to 5 minutes, at temperature between 25 and 55° C.).

Oligonucleotide Probes

Oligonucleotide probes according to the present disclosure are those having between about 1 nucleotide to about 100 nucleotides. Exemplary oligonucleotide probes include between about 1 nucleotide to about 20 nucleotides, between about 3 nucleotides to about 15 nucleotides, between about 5 nucleotide to about 12 nucleotides or between about 6 nucleotide to about 10 nucleotides. An exemplary oligonucleotide probe includes about 6 nucleotides. According to one aspect, oligonucleotide probes according to the present disclosure should be capable of hybridizing to the single stranded nucleic acid template.

According to an additional aspect, oligonucleotide probes according to the present disclosure should be capable of hybridizing to the single stranded nucleic acid template and ligating to a sequencing primer or an extended duplex to generate the extended duplex for the next ligation cycle. According to a still additional aspect, a combination of oligonucleotide probes can be used where a first probe is capable of hybridizing to the single stranded nucleic acid template and ligating to a sequencing primer or an extended duplex to generate the extended duplex for the next ligation cycle and a second probe is capable of hybridizing to the single stranded nucleic acid template. Probes according to the present disclosure may include a detectable moiety or may be capable of being rendered detectable. Oligonucleotide probes may be designed with the aid of a computer program such as, for example, DNAWorks, or Gene2Oligo.

Oligonucleotide probes according to the present disclosure may include a terminal moiety which prevents multiple ligations in a single ligation cycle. Oligonucleotide probes according to the present disclosure should also be capable of being modified to create or include an extendable terminus for further ligation if an extendable terminus is not already present. Oligonucleotide probes according to the present disclosure need not form a perfectly matched duplex with the single stranded nucleic acid template, though a perfect matched duplex is exemplary. Instead, oligonucleotide probes need only have a perfect match between a nucleotide in the probe and the complementary nucleotide being identified by the methods described herein.

Hybridization and Ligation of Oligonucleotide Probes

Methods of hybridizing and ligating oligonucleotide probes to a single stranded template nucleic acid are known to those of skill in the art. "Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* 1$^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include T4 DNA ligase, T7 DNA ligase, *E. coli* DNA ligase, Taq ligase, Pfu ligase and the like. Certain protocols for using ligases are disclosed by the manufacturer and also in Sambrook, Molecular Cloning: A Laboratory manual, $2^{nd}$ Edition (Cold Spring Harbor Laboratory, New York, 1989); barany, PCR Methods and Applications, 1:5-16 (1991); Marsh et al., Strategies, 5:73-76 (1992).

If ligation is not 100% efficient, it may be desirable to cap extended duplexes that fail to undergo ligation so that they do not participate in further ligation steps. According to certain aspects, capping can be done by removing the 5'phosphate (5'PO) using an alkaline phosphatase. By example, following ligation of the oligonucleotide probes for sequencing, unreacted 5'PO are removed by adding an alkaline phosphatase in solution, such as 10 units of calf insetting alkaline phosphatase (NEB #M0393L) in 100 µL of its reaction buffer. The reaction is incubated for 15 minutes at room temperature. Other alkaline phosphatases are suitable. Capping can also be done by using a polymerase, deficient in exonuclease activity, to add a terminal nucleotide in the 5'->3' direction (so capping the 3' end of a primer). Terminal nucleotide varies but most frequently used are dideoxynucleotides (ddNTP) and acyclonucleotides (acyNTP). A nontemplated nucleotide can also be used as a terminal nucleotide. Capping by polymerase extension is performed as described to amplify a polynucleotide sequence using DNA polymerases, except that dNTP normally used in the reaction are substituted by terminal NTP (e.g. ddNTP), which prevent the DNA polymerase or Terminal Transferase (TdT) of adding more than one nucleotide. By example, following ligation of the oligonucleotide probes for sequencing, a capping mix is added, which consists of 1 mM of ddNTP and 20 units of Terminal Transferase (NEB #M0315L) in 100 µL of its reaction buffer. The reaction is incubated for 15 minutes at room temperature. Alternatively, capping can be done by ligating an oligonucleotide, ideally between 6-9mer long, with a capped end. The cap can be in the form of 5'hydroxyl (5'OH), instead of 5'PO, and oppositely 3'PO instead of 3'OH, a terminal NTP (ddNTP, inverted ddNTP, acyNTP) or an oligo with a terminal carbon spacer (e.g. C3 spacer). This method would work as well for capping the 5'end or the 3'end of the polynucleotyde sequence to be capped. Capping by ligation is performed as described for ligating an oligonucleotide probe. By example, following ligation of the oligonucleotide probes for sequencing, a capping mix is added, which consists of 1 uM of a 5'- or 3'-capped oligonucleotide added to the ligation buffer with 1200 units of T4 DNA ligase, per 100 µL reaction volume. The reaction is incubated for 15 minutes at room temperature.

According to the present disclosure, a specific set of oligonucleotide probes L1 is utilized to hybridize to the ssDNA template and covalently linked to the sequencing primer P1 by a DNA ligase. Oligonucleotide probes L1 are prepared in ligation buffer (typically at 1 uM), and ligated using 6000 units of T3 DNA ligase (Enzymatics #L601L) or 1200 units of T4 DNA ligase (Enzymatics #L603-HC-L) per 100 µL reaction volume. The reaction is allowed to incubate at room temperature for a few minutes to several hours (typically between 5 minutes to 2 hours, at a temperature between 15° C. and 35° C.). Then the enzymes and any unligated oligonucleotide probes L1 are washed away with wash 1 buffer.

Hybridization Conditions

In certain exemplary embodiments, the terms "annealing" and "hybridization," as used herein, are used interchangeably to mean the formation of a stable duplex. In one aspect, stable duplex means that a duplex structure is not destroyed by a stringent wash under conditions such as a temperature of either about 5° C. below or about 5° C. above the $T_m$ of a strand of the duplex and low monovalent salt concentration, e.g., less than 0.2 M, or less than 0.1 M or salt concentrations known to those of skill in the art. The term "perfectly matched," when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" includes, but is not limited to, the pairing of nucleoside analogs, such as deoxyinosine, nucleosides with 2-aminopurine bases, PNAs, and the like, that may be employed. A "mismatch" in a duplex between two oligonucleotides means that a pair of nucleotides in the duplex fails to undergo Watson-Crick bonding.

As used herein, the term "hybridization conditions," will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, e.g., conditions under which a probe will specifically hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual*, 2nd Ed. Cold Spring Harbor Press (1989) and Anderson *Nucleic Acid Hybridization*, $1^{st}$ Ed., BIOS Scientific Publishers Limited (1999). As used herein, the terms "hybridizing specifically to" or "specifically hybridizing to" or similar terms refer to the binding, duplexing, or hybridizing of a molecule substantially to a particular nucleotide sequence or sequences under stringent conditions.

Template Non-Hybridizing Nucleic Acid Sequences

According to certain aspects of the present disclosure, a template non-hybridizing nucleic acid sequence is attached to an oligonucleotide probe. The template non-hybridizing nucleic acid sequence may include a detectable moiety, label or reporter. The template non-hybridizing nucleic acid sequence may include a probe hybridization site for hybridizing with a probe having a detectable moiety, label or reporter. The template non-hybridizing nucleic acid sequence may be a linear nucleic acid sequence or the template non-hybridizing nucleic acid sequence may be in a stem and loop configuration.

Methods of making linear nucleic acid sequences are known to those of skill in the art. The linear nucleic acid sequence is designed to include one or more or a plurality of probe hybridization sites with the nucleic acid sequences for the probe hybridization sites being selected to be complementary to probe nucleic acid sequences thereby resulting in hybridization of the probe to the probe hybridization site. According to one aspect, linear nucleic acid sequences can be designed by selecting a sequence of nucleotides and then determining Watson-Crick base pairings using methods and algorithms such as those described in Zuker et al., Algorithms and Thermodynamics for RNA Secondary structure Prediction: A Practical Guide, RNA Biochemistry and Biotechnology, p. 11-43, J. Barciszewski and B. F. C. Clark, eds., NATO ASI Series, Kluwer Academic Publishers, Dordrecht, NL (1999). For sequences that have a high likelihood of forming base pairing, nucleotides may be changed. The probe includes a detectable moiety, label or reporter and so the template non-hybridizing nucleic acid sequence would include a detectable moiety, label or reporter when the probe is hybridized to the corresponding probe hybridization site.

Methods of making stem and loop nucleic acid configurations are known to those of skill in the art. The loop configuration is designed to include one or more or a plurality of probe hybridization sites with the nucleic acid sequences for the probe hybridization sites being selected to be complementary to probe nucleic acid sequences thereby resulting in hybridization of the probe to the probe hybridization site. According to one aspect, stem and loop nucleic acid configurations can be designed by selecting a sequence of nucleotides and then determining Watson-Crick base pairings using methods and algorithms such as those described in Zuker et al., Algorithms and Thermodynamics for RNA Secondary structure Prediction: A Practical Guide, RNA Biochemistry and Biotechnology, p. 11-43, J. Barciszewski and B. F. C. Clark, eds., NATO ASI Series, Kluwer Academic Publishers, Dordrecht, NL (1999). For sequences that have a high likelihood of forming base pairing, nucleotides may be changed. The probe includes a detectable moiety, label or reporter and so the template non-hybridizing nucleic acid sequence would include a detectable moiety, label or reporter when the probe is hybridized to the corresponding probe hybridization site.

The probe includes a detectable moiety, label or reporter and so the template non-hybridizing nucleic acid sequence would include a detectable moiety, label or reporter when the probe is hybridized to the corresponding probe hybridization site. The stem and loop configuration may include a detectable moiety, label or reporter directly attached to the stem and loop configuration. Methods of attaching a detectable moiety, label or reporter to a nucleic acid sequence are known to those of skill in the art.

Detectable Moieties

In certain exemplary embodiments, a detectable moiety, label or reporter can be used to detect one or more nucleotides described herein. Oligonucleotides described herein can be labeled in a variety of ways, including the direct or indirect attachment of a detectable moiety such as a fluorescent moiety, colorimetric moiety and the like. One of skill in the art can consult references directed to labeling DNA. Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$ $^{14}C$, or $^{3}H$. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology*, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY FL-14-UTP, BODIPY TMR-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Alternatively, the above fluorophores and those mentioned herein may be added during oligonucleotide synthesis using for example phosphoroamidite or NHS chemistry. Protocols are known in the art for custom synthesis of nucleotides having other fluorophores (See, Henegariu et al. (2000) *Nature Biotechnol.* 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g. SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, Oreg.), Cy2, Cy3, Cy3.5, Cy5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

Metallic silver or gold particles may be used to enhance signal from fluorescently labeled nucleotide and/or oligonucleotide sequences (Lakowicz et al. (2003) *BioTechniques* 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP or aminohexylacrylamide-dCTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for an oligonucleotide sequence may include fluorescein (FAM, FITC), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

According to certain aspects, detectable moieties described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

Cleavable Moieties

According to certain aspects of the present disclosure, cleavable nucleotide moieties also referred to as cleavable linkages are used to separate an oligonucleotide probe from a template non-hybridizing nucleic acid structure. Cleavable moieties are known to those of skill in the art and include chemically scissile internucleosidic linkages which may be cleaved by treating them with chemicals or subjecting them to oxidizing or reducing environments. Such cleavable moieties include phosphorothioate, phosphorothiolate which can be cleaved by various metal ions such as solutions of silver nitrate. Such cleavable moieties include phosphoroamidate which can be cleaved in acidic conditions such as solutions including acetic acid. A suitable chemical that can cleave a linkage includes a chemical that can cleave a bridged-phosphorothioate linkage and can remove a phosphoramidite linker from a nucleotide and/or oligonucleotide, leaving a free phosphate group on the nucleotide and/or oligonucleotide at the cleavage site. Suitable chemicals include, but are not limited to $AgNO_3$, $AgCH_3COO$, $AgBrO_3$, $Ag_2SO_4$, or any compound that delivers $Ag^{2+}$, $HgCl_2$, $I_2$, $Br_2$, $I^-$, $B^-$ and the like.

Cleavable moieties also include those that can be cleaved by nucleases known to those of skill in the art. Such nucleases include restriction endonucleases such as Type I, Type II, Type III and Type IV, endonucleases such as endonucleases I-VIII, ribonucleases and other nucleases such as enzymes with AP endonuclease activity, enzymes with AP lyase activity and enzymes with glycosylase activity such as uracil DNA glycosylase.

Cleavable moieties also include those capable of being cleaved by light of a certain wavelength. Such cleavable moieties are referred to as photolabile linkages and are disclosed in Olejnik et al., Photocleavable biotin derivatives: a versatile approach for the isolation of biomolecules, *Proc. Natl. Acad. Sci. U.S.A.*, vol. 92, p. 7590-7594 (1995). Such photocleavable linkers can be cleaved by UV illumination between wavelengths of about 275 to about 375 nm for a period of a few seconds to 30 minutes, such as about one minute. Exemplary wavelengths include between about 300 nm to about 350 nm.

Certain nucleotides, such as dGTP, dCTP and dTTP could also be reacted before being incorporated for use as a cleavable linkage, making them specifically sensitive to further cleavage by nucleases or chemicals. According to one aspect, one or multiple deoxyguanosines in a given template non-hybridizing nucleic acid can be oxidized to 8-oxo-deoxyguanosine by 2-nitropropane, before being added to the sequencing reaction, and subsequently cleaved using an 8-oxoguanine DNA glycosylase (e.g. Fpg, hOGG1). Similarly, deoxycytosines can be pre-reacted to form 5-hydroxycytosine, using bisulfite or nitrous acid, which can then be processed by certain DNA-glycosylase, such as hNEIL1. Other nucleotides which can be cleaved include uracil, deoxyuridine, inosine and deoxyinosine.

Additional embodiments include nucleotides that may be cleaved in a two step method such as by a first step that modifies the nucleotide making it more susceptible to cleavage and then a second step where the nucleotide is cleaved. Such systems include the USER system (commercially available from Enzymatics (#Y918L) or New England Biolabs (#M5505L) which is typically a combination of UDG and Endonuclease VIII, although other endonucleases could be used. Enzymes UDG and endonuclease are commercially available. In addition, modified nucleotides may be cleavable nucleotides where a feature of the nucleotide has been modified, such as a bond, so as to facilitate cleavage. Examples include an abasic base, an apyrimidic base, an apurinic base, phosphorothioate, phosphorothiolate and oxidized bases such as deoxyguanosines which can be oxidized to 8-oxo-deoxyguanosine.

Accordingly, internucleotide bonds may be cleaved by chemical, thermal, or light based cleavage. Exemplary chemically cleavable internucleotide linkages for use in the methods described herein include, for example, β-cyano ether, 5'-deoxy-5'-aminocarbamate, 3'deoxy-3'-aminocarbamate, urea, 2'cyano-3', 5'-phosphodiester, 3'-(S)-phosphorothioate, 5'-(S)-phosphorothioate, 3'-(N)-phosphoramidate, 5'-(N)-phosphoramidate, α-amino amide, vicinal diol, ribonucleoside insertion, 2'-amino-3',5'-phosphodiester, allylic sulfoxide, ester, silyl ether, dithioacetal, 5'-thio-furmal, α-hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include β-cyano ether, 5'-deoxy-5'-aminocarbamate, 3'-deoxy-3'-aminocarbamate, urea, 2'-cyano-3', 5'-phosphodiester, 2'-amino-3', 5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium may be used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

Accordingly, internucleotide bonds may be cleaved using enzymatic cleavage. Nucleic acid sequences described herein may be designed to include a restriction endonuclease cleavage site. A nucleic acid may be contacted with a restriction endonuclease to result in cleavage. A wide variety of restriction endonucleases having specific binding and/or cleavage sites are commercially available, for example, from New England Biolabs (Ipswich, Mass.). In various embodiments, restriction endonucleases that produce 3' overhangs, 5' overhangs or blunt ends may be used. When using a restriction endonuclease that produces an overhang, an exonuclease (e.g., $RecJ_f$, Exonuclease I, Exonuclease T, $S_1$ nuclease, $P_1$ nuclease, mung bean nuclease, CEL I nuclease, etc.) may be used to produce blunt ends. In an exemplary embodiment, an orthogonal primer/primer binding site that contains a binding and/or cleavage site for a type IIS restriction endonuclease may be used to remove the temporary orthogonal primer binding site.

As used herein, the term "restriction endonuclease recognition site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type IIS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) Nucl. Acids Res. 33:D230, incorporated herein by reference in its entirety for all purposes).

In certain aspects, primers of the present invention include one or more restriction endonuclease recognition sites that enable type IIS enzymes to cleave the nucleic acid several base pairs 3' to the restriction endonuclease recognition sequence. As used herein, the term "type IIS" refers to a restriction enzyme that cuts at a site remote from its recognition sequence. Type IIS enzymes are known to cut at a distances from their recognition sites ranging from 0 to 20 base pairs. Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.). Information about the recognition sites, cut sites and conditions for digestion using type IIs endonucleases may be found, for example, on the Worldwide web at neb.com/nebecomm/enzymefindersearch bytypeIIs.asp). Restriction endonuclease sequences and restriction enzymes are well known in the art and restriction enzymes are commercially available (New England Biolabs, Ipswich, Mass.).

According to certain aspects, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., Ann. Rev. Biochem. 67:99-

134 (1998); U.S. Pat. Nos. 5,739,386, 5,700,642 and 5,830,655; and U.S. Patent Publication Nos. 2003/0186226 and 2004/0106728).

The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N) phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOPS™ phosphoramidite. Conditions for Universal TOPS™ phosphoramidite preparation, coupling and cleavage are detailed, for example, in Hardy et al. *Nucleic Acids Research* 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., *J. Org. Chem.* 61:525-529 (1996), Kahl et al., *J. Org. Chem.* 64:507-510 (1999), Kahl et al., *J. Org. Chem.* 63:4870-4871 (1998), Greenberg et al., *J. Org. Chem.* 59:746-753 (1994), Holmes et al., *J. Org. Chem.* 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially.

Certain Embodiment 1

With reference to FIGS. 1A, 2A, 4A and 5A, oligonucleotide L1 is composed of a hexamer, which hybridizes to the single stranded nucleic acid template and is ligated to the sequencing primer P1. This hexamer is composed of N nucleotides, with nucleotide N1 being the most proximal to sequencing primer P1 and nucleotide N6 the most distal. Nucleotide N6 is attached to the template nonhybridizing nucleic acid structure TNH via cleavage moiety C1. According to one aspect where a hexamer oligonucleotide probe L1 is used, 4096 hexamer oligonucleotide probes ($4^6$=4096) are prepared such that all the nucleotides (A, C, G or T) are known at each of the N positions in every combination possible. In FIGS. 1A, 2A, 4A and 5A, the template nonhybridizing nucleic acid structure will have 6 barcode recognition sites B1 to B6, of which a complementary oligo barcode probe BP1 to BP6 will hybridize. This provides information about the identity of all nucleotides N1 to N6. This aspect of the present disclosure allows the identification of all nucleotides N in the hexamer and to associate this information to the complementary paired nucleotides on the single stranded nucleic acid template.

With reference to FIGS. 3 and 6, oligonucleotide probe L1 is composed of a hexamer, which hybridizes to the single stranded nucleic acid template and is ligated to sequencing primer P1. This hexamer is composed of N nucleotides, with nucleotide N1 being the most proximal to sequencing primer P1 and nucleotide N6 being the most distal. Nucleotide N6 is attached to the template nonhybridizing nucleic acid structure TNH via cleavage moiety C1. The template nonhybridizing nucleic acid structure TNH includes the reporter moiety R1. According to this aspect of the present disclosure, a total of 24 oligonucleotide probes are required for sequencing. For position N1, four probes are designed having a known nucleotide A, C, G, or T with the remaining nucleotides N2 to N6 being unknown. A detectable moiety or label or reporter R1 is selected for each probe to identify the known nucleotide at position N1. For position N2, four probes are designed having a known nucleotide A, C, G, or T with the remaining nucleotides N1 and N3 to N6 being unknown. A detectable moiety or label or reporter R1 is selected for each probe to identify the known nucleotide at position N2. This probe design is repeated for each of N3 to N6 thereby resulting in a total of 24 oligonucleotide probes L1, i.e. 6 sets of 4 oligos, i.e. one set for each position from N1 to N6. This aspect allows the identification of each nucleotide in the hexamer and to associate this information to the complementary paired nucleotide on the single stranded template nucleic acid.

With reference to FIGS. 1, 2, 4, 5, 7, and 11, oligonucleotide probe L1 is composed of a hexamer, which hybridizes to the single stranded nucleic acid template and is ligated to sequencing primer P1. This hexamer is composed of N nucleotides, with nucleotide N1 being the most proximal to sequencing primer P1 and nucleotide N6 being the most distal. Nucleotide N6 is attached to the template nonhybridizing nucleic acid structure TNH via cleavage moiety C1. The template nonhybridizing nucleic acid structure TNH includes a barcode recognition site B1. A total of 24 oligonucleotide probes L1 are required for sequencing, i.e. 6 sets of 4 oligos as in FIG. 3, with each set corresponding to a specific nucleotide N position, by the way of a barcode recognition sequence (i.e. barcode B1 corresponds to N1 in a given set, barcode B2 corresponds to N2 in a second set, and so on). The hexamer on each one of the 24 oligonucleotide probes L1 is designed such that one of nucleotides (A, C, G or T) is known at a given N position, hence oligonucleotide probe L1 is composed of a set of 24 oligonucleotide probes (4*6=24). This aspect allows the identification of all N in the hexamer and to associate this information to the complementary paired nucleotides on the single stranded template nucleic acid.

With reference to FIGS. 5 and 5A, the distal hybridizing strand serves as a ligation site to assemble multiple oligonucleotide probes L1 directly on the template. In one embodiment, an oligonucleotide probe L1-chain is formed by repeated cycles of ligation on the template prior to sequencing by hybridization using labeled barcode probes. In another embodiment, oligonucleotide probe L1-chain is formed on the bound template prior to sequencing. In another embodiment, oligonucleotide probe L1-chain is formed after each sequencing step. In one embodiment, oligonucleotide probe L1-chain can be self-assembled, i.e. an equimolar mix of up to 4096 oligonucleotide probe L1, with a 5'-$PO_4$, is hybridized to the template in the presence of a DNA ligase or chemical ligation. In another embodiment, oligonucleotide probe L1-chains are formed successively, i.e. by hybridizing and ligating a given oligonucleotide probe L1 to sequencing primer P1, followed by washing and phosphorylation or deprotection, ligating a second oligonucleotide probe L1 to the ligated P1-L1 complex, and so on.

With reference to FIGS. 3, 6, and 10, oligonucleotide probe L1 is hybridized to the single stranded DNA (ssDNA) template and covalently linked to the sequencing primer by a DNA ligase. A total of 24 oligonucleotide probes L1 are required for sequencing each of the 6 nucleotides in the hexamer. For each nucleotide at a given position N, the detectable moiety or label or reporter is one of four fluorophores, such that each set will be detected in four different colors of the electromagnetic spectrum, and will be later associated to one of each nucleotides (e.g. A green, C orange, G blue or T red).

Oligonucleotide probe L1 in each set are mixed as an equal molar ratio before use (e.g. 25 µM each). The template is interrogated in a serial way (i.e. from N1 to N6), but need not be. The set of oligonucleotide probes L1 with the known nucleotides N1 is hybridized to the ssDNA and covalently joined to P1 by a DNA ligase. Upon detection, each color is associated to a nucleotide (A, C, G or T) at position N1. By example, if on a given template the green spectrum is detected, nucleic acid A at identified at N1, and the complementary paired base T is identified on the single stranded nucleic acid template.

After detection, the labeled template nonhybridizing nucleic acid structure TNH is separated at C1 from its hexamer, leaving a terminal group ready to be covalently linked during a second round of ligation. The second round of ligation uses the same set of oligonucleotide probes L1 that was used in the first round, as described above. This allows identifying NT7 on the ssDNA template. The cleavage and ligation series can be repeated as many time as needed, allowing to identify NT13 after the $3^{rd}$ series, NT19 after the $4^{th}$ series, and so on.

Afterward, the now extended sequencing primer P1 is stripped from the template using denaturing conditions. This can be accomplished by increasing the temperature with or without the use of denaturing agents such as NaOH, Urea, Guanidium thiocyanate, Formamide or Dymethyl sulfoxide. Typically, 65% formamide is used in TE at room temperature and incubate for 1 to 2 minutes. Then, formamide and the extended primer is washed away with Wash 1 buffer.

To identify the template nucleotide 2 (NT2), sequencing primer P1 is hybridized to the template nucleic acid. The second set of oligonucleotide probes L1 is ligated where nucleotide N2 is known. Then, a series of detection, cleavage and ligation is repeated, using the same set of oligonucleotide probes L1 to identify template nucleotide 8 (NT8). This can be repeated as many time as needed, allowing the identification of NT14 after the $3^{rd}$ series, NT20 after the $4^{th}$ series, and so on.

Stripping and probing are repeated to serially identify all remaining N3 to N6 and their corresponding nucleotides on the ssDNA template.

Certain Embodiment 2

With reference to FIGS. 1, 2, 4, 5, 7, and 11, a portion of oligonucleotide L1 is hybridized to the ssDNA template and covalently linked to the sequencing primer by a DNA ligase. A total of 24 oligonucleotide probes L1 are required for sequencing. Moreover, reporter R1 for a given set is one of four fluorophores, such that each set will be detected in four different color of the electromagnetic spectrum, and will be later associated to one of each nucleotides (e.g. A green, C orange, G blue or T red).

Each oligonucleotide probe set is prepared as an equal molar ratio before use (e.g. 1 µM each). The template may be interrogated in a serial way (i.e. from N1 to N6), but need not be. The set is hybridized to the ssDNA and covalently joined to sequencing primer P1 by a DNA ligase.

Then, a set of four R1-labelled probes (BP1) is then added to hybridize with probe hybridization site B1. Each set of BPs is designed such that it is specifically related to the identification of one of the nucleotides N, such that BP1 is composed of four R1-labelled 12mer oligonucleotides used to identify nucleotide N1, BP2 is composed of four R1-labelled 12mer oligonucleotides used to identify nucleotide N2, and so on.

Hybridization of barcode probe BP1 to probe hybridization site B1 can be performed in any suitable buffer. While Wash 1 buffer could be used, more ionic buffer, especially Na+ (e.g. PBS, 5×SSPE, Bind & Wash) or $Mg^{2+}$ (Folding buffers) are preferred. In one example, 1 uM labeled probes in 5×SSPE are hybridized with the template non-hybridizing nucleic acid structure for a few seconds to a few minutes (typically 1 or 2 minutes). Afterward, nonhybridized labeled probes are washed away using 5×SSPE, and the remainder are detected.

Upon detection, each color is associated to a nucleotide (A, C, G or T) at position N1. By example, if on a given template the green spectrum is detected, an A at N1 is identified and correspondingly the complementary paired base T on NT1 is identified.

After detection, the set of BP1 is washed away using TE buffer.

Afterward the template non-hybridizing nucleic acid structure is separated at C1 from the oligonucleotide hexamer probe L1.

The second round of ligation uses the same set of four L1 that was used in the first round, as described above. It is also probed with the same set of four BP1 as described above. This would allow identifying NT7 on the ssDNA template. The cleavage, ligation and hybridization series can be repeated as many times as needed to identify NT13 after the $3^{rd}$ series, NT19 after the $4^{th}$ series, and so on.

Afterward, this extended sequencing primer P1 is stripped from the template.

To identify the template nucleotide 2 (NT2), sequencing primer P1 is hybridized to the template nucleic acid. A different set of four oligonucleotide probes L1 is the ligated, by example the set of L1 designed to identify N2. The set of four BP1 used with the first set of L1 is then hybridized as described above. Identification is performed as described above. This allows identification of NT2. The series of cleavage, ligation, hybridization and detection is then repeated using this same set of L1 to identify NT8 on the template. This can be repeated as many time as needed, allowing the identification of NT14 after the $3^{rd}$ series, NT20 after the $4^{th}$ series, and so on.

Stripping and probing are repeated to serially identify the remaining N3 to N6 positions of the hexamer and their corresponding nucleotides on the ssDNA template.

Certain Embodiment 3

Referring to FIGS. 1A, 2A, 4A and 5A, a portion of oligonucleotide probe L1 is hybridized to the ssDNA template and covalently linked to the sequencing primer by a DNA ligase, as described in Example IV. The template non-hybridizing nucleic acid structure includes probe hybridization sites. A total of 4096 oligonucleotide probes L1 are required for sequencing. Moreover, reporter R1 in each of four oligonucleotide probes for a given set is one of four fluorophores, such that each set will be detected in four different colors of the electromagnetic spectrum, and will be later associated to one of each nucleotides (e.g. A green, C orange, G blue or T red).

L1 set is mixed as an equal molar ratio before use (e.g. 0.2 μM each). The template is interrogated in a serial way (i.e. from N1 to N6), but need not be. The set is hybridized to the ssDNA and covalently joined to P1 by a DNA ligase, with a final concentration of 0.1 uM.

Six sets of four labeled barcode probes (BP1-BP6) are then successively added to hybridize B1-B6 of the template non-hybridizing nucleic acid structure (total of 24 labeled BPs). Each set is designed such that it is specifically related to the identification one of the N, such that BP1 is composed of four R1-labelled 12mer oligonucleotide probes used to identify N1, BP2 is composed of four R1-labelled 12mer oligonucleotide probes used to identify N2, and so on.

Hybridization of BP1 to B1 can be performed in any suitable buffer. While Wash 1 buffer could be used, more ionic buffer, especially Na+ (e.g. PBS, 5×SSPE, Bind & Wash) or Mg2+ (Folding buffers) are preferred. In one example, an equal molar mix of 1 μM BP1 in 5×SSPE are hybridized with the template non-hybridizing nucleic acid structure for a few seconds to a few minutes (typically 1 or 2 minutes). Afterward, nonhybridized BP1 are washed away using 5×SSPE.

Upon detection, each color is associated to a nucleotide (A, C, G or T) at position N1. By example, if on a given template the green spectrum is detected, an A at N1 is identified and correspondingly the complementary paired base T on NT1 is identified.

After detection, the set of BP1 are washed away using TE buffer. Then, BP2 is hybridized to B2 and detected. If, for the same template, the blue spectrum is detected, which corresponds to a G, a C at NT2 is identified, following the A previously identified in NT1. The series of wash, hybridization and detection steps are repeated for the remaining N3 to N6 positions. This way we identify nucleotides NT1 to NT6.

Afterward the template non-hybridizing nucleic acid structure is separated at C1 from the oligonucleotide hexamer probe L1.

The second round of ligation uses the same 4096 set of L1 that was used for the first round, as described above. It is also probed serially using the six sets of BP1 to BP6. This would allow identifying NT7 to NT12. This can be repeated as many time as needed, allowing one to identify a total of 18 nucleotides if 3 series of cleavage, ligation, hybridizations and detection are performed, 24 nucleotides if 6 series are performed, 60 nucleotides if 10 series are performed, and so on.

Buffers

All buffers are prepared in distilled or deionized water (DI water), pH is adjusted at room temperature using NaOH, KOH or HCl if necessary, and then sterilized by passing through a filter (0.22 to 0.45 μM mesh) or by autoclaving, unless otherwise indicated. 1% aminosilane (v/v): 1 volume of 3-Aminopropyltriethoxysilane (Pierce #80370 or Sigma #A3648) added to 99 volumes of DI water, or acetone. Do not sterilize. Use immediately. Bind and Wash buffer: 5 mM Tris-HCl pH 7.5, 0.5 mM EDTA ph 8.0, 1.0 M NaCl. Folding buffer 1: 5 mM Tris-HCl, pH 7.5, 0.5 mM EDTA, 12.5 mM $MgCl_2$. Folding buffer 2: 20 mM Tris base, 10 mM acetic acid, 0.5 mM EDTA, 12.5 mM Magnesium-acetate. Ligation buffer: 50 mM Tris-HCl. 10 mM $MgCl_2$, 5 mM dithiothreitol, 1 mM ATP, pH 7.6. PBS buffer pH 7.4: 137 mM NaCl, 2.68 mM KCl, 10 mM $Na_2HPO_4$, 1.76 mM $KH_2PO_4$. 5×SSPE buffer: 750 mM NaCl, 50 mM $Na_2HPO_4$, 5 mM EDTA, pH 7.4. TE buffer: 10 mM Tris-HCl pH 8.0, 1 mM EDTA pH 8.0. Wash 1 buffer: 10 mM Tris.Cl pH 7.5, 50 mM KCl, 2 mM EDTA pH 8.0, 0.01% Triton X-100 (v/v).

Example I

Rolony templates to be sequenced were prepared using synthetic templates ordered from the company IDT and resuspended in TE at 100 The synthetic ssDNA sequences were: 3 pA, /5PHOS/GTT CCT CAT TCT CTG AAG A NNA NNC NNG NNT NNA NNC CNN ANN TNN GNN CNN ANN ACT TCA GCT GCC CCG G (SEQ ID NO: 26); 3pC, /5PHOS/GTT CCT CAT TCT CTG AAG A NNC NNG NNT NNA NNC NNG GNN CNN ANN TNN GNN ANN ACT TCA GCT GCC CCG G (SEQ ID NO:27); 3pG, /5PHOS/GTT CCT CAT TCT CTG AAG A NNG NNT NNA NNC NNG NNT TNN GNN CNN ANN TNN ANN ACT TCA GCT GCC CCG G (SEQ ID NO:28); 3pT, /5PHOS/GTT CCT CAT TCT CTG AAG A NNT NNA NNC NNG NNT NNA ANN TNN GNN CNN ANN ANN ACT TCA GCT GCC CCG G (SEQ ID NO:29).

These ssDNA template were circularized separately using Circligase II kit from Epicentre #CL9025K. 10 U of Circligase II enzyme was added in a total reaction volume of 20 μL containing 10 pmol of template and incubated at 60° C. for 1 h. The reaction was terminated by incubating at 80° C. for 10 min. Non-circularized product, if any, where digested by adding 20 U of Exonucleases I (Enzymatics #X801L) and 100 U of Exonuclease III (Enzymatics III), and incubated at 37° C. for 45 min, and terminated by incubating at 80° C. for 15 min. The circular products were purified using the MinElute PCR purification column and reagents (QIAgen #28004).

The circularized ssDNA templates were amplified separately by RCA using phi29 DNA polymerase kit (Enzymatics #P702L). 10 U of phi29 DNA polymerase was used in a total reaction volume of 50 µL containing approximately 1 pmol of the circularized template and 1 pmol RCA primer (IDT: AAT GAG GAA CCC GGG GCA*G*C) (SEQ ID NO:30), and incubated at 30° C. for 2 h. 450 µL of 1×PBS was added to stop the reaction. Rolony were kept at 4° C. until needed.

A piece of silicon 5×2 cm, was cut from a silicon wafer (SVM), then immersed for 30 min in a solution containing 1% vol/vol 3-Aminopropyltriethoxysilane (Sigma #A3648). This aminosilane treated silicon was rinsed with distilled water and dried using compressed air. Two strips of double sided tape (3M Scotch) were disposed parallel to each other approximately 1 cm apart, and a microscope cover slip (VWR #16004-344) was disposed on top of the tape to create a linear flow cell.

The four Rolony templates were mixed and further diluted 1:10 in 1×PBS. Approximately 60 µL were loaded in the flow cell and let bound for 30 min. Then the unbound Rolony were washed with 500 µL of Wash 1.

100 uL of sequencing primer mix [2 µM of sequencing primer (IDT: /5PHOS/ACT TCA GCT GCC CCG GGT) (SEQ ID NO:31) in 5×SSPE], where loaded in the flow cell, which was then incubated at 50° C. for 1 min and let to cool at room temperature for 5 min.

A set of 4 labelled-oligonucleotide hairpin probes where used, in which N3 was known and used to interrogate NT3, NT9 and NT15 on the template: Hrp-M3A, /5TYE563/AC GCT GGA ACA GCG/ideoxyU/NNN ANN (SEQ ID NO:32); Hrp-M3C, /5TEX615/AC GCT GGA ACA GCG/ideoxyU/NNN CNN (SEQ ID NO:33); Hrp-M3G, /56-FAM/AC GCT GGA ACA GCG/ideoxyU/NNN GNN (SEQ ID NO:34); Hrp-M3T, /5TYE665/AC GCT GGA ACA GCG/ideoxyU/NNN TNN (SEQ ID NO:35).

Oligo probes were mixed in an equimolar ratio. 100 µL of ligation mix [50 mM Tris-HCl, 10 mM MgCl$_2$, 5 mM dithiothreitol, 1 mM ATP, 4 uM of oligo probe mix and 1200 U T4 DNA ligase (Enzymatics #L603-HC-L)] was loaded in the flow cell and incubated at room temperature for 30 min. The unligated oligo probes were washed using 500 µL of Wash 1.

The flow cell was imaged in the Polonator G.007 (Dover, a Danaher company), to identify NT3.

After imaging, the unligated sites, which consist of 5' phosphorylated sequencing primers, were capped using calf intestine alkaline phosphatase (NEB #M0290L). 100 µL of phosphatase mix [50 mM Tris-HCl, 100 mM NaCl, 10 mM MgCl$_2$, 1 mM dithiothreitol and 50 U alkaline phosphatase] was loaded in the flow cell and incubated at room temperature for 30 min. The enzyme was then washed out with 500 µL of Wash 1.

After capping, the deoxyuridine in the hairpin structure was cleaved using the 10× Uracil Cleavage System (Enzymatics #Y918L). 100 µL of uracil cleavage mix [50 mM Tris-HCl, 100 mM NaCl, 10 mM MgCl$_2$, 1 mM dithiothreitol, 40 U of UDG and 200 U of Endo VIII] were loaded in the flow cell and incubated at room temperature for 30 min. Then the flow cell was washed with 500 µL of Wash 1.

The ligation, imaging, capping and cleavage were repeated as described two more time, with the same set of oligo probes, to successively identify NT9 and NT15. The results are presented in FIGS. 8A, 8B, 9A, and 9B.

Figure 8A:
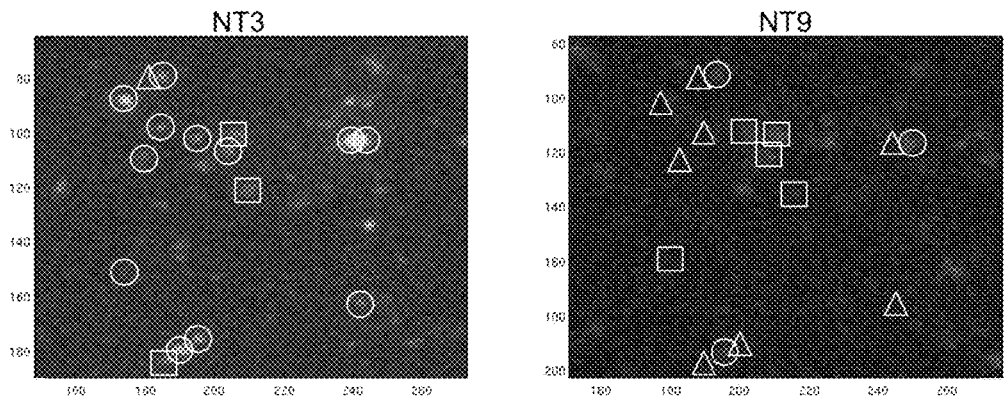
FIG. 8A is a grayscale picture of a three-color image of Rolony sequenced as described in Example I. Interrogation of the $3^{rd}$ (left image) and $9^{th}$ positions (right image) downstream of the sequencing primer site on the ssDNA template. Geometrical shapes as indicated in the legend mark Rolony that are common in both images. Base change between two positions can be observed by shape change. Only a small portion of the original images are shown and enlarged 16 times.

FIG. 8A is a grayscale picture of a three-color image of Rolony sequenced as described in Example I. Interrogation of the 3$^{rd}$ (left image) and 9$^{th}$ positions (right image) downstream of the sequencing primer site on the ssDNA template. Geometrical shapes as indicated in the legend mark Rolony that are common in both images. Base change between two positions can be observed by shape change. Only a small portion of the original images are shown and enlarged 16 times.

Figure 8B:
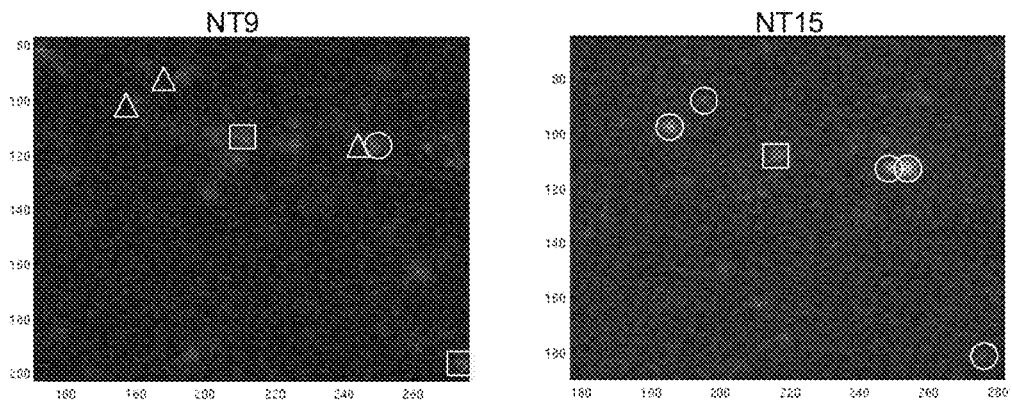
FIG. 8B is a grayscale picture of a three-color image of Rolony sequenced as described in Example I. Interrogation of the $9^{th}$ (left image) and $15^{th}$ positions (right image) downstream the sequencing primer site on the ssDNA template. Geometrical shapes as indicated in the legend mark Rolony that are common in both images. Base change between two positions can be observed by shape change. Only a small portion of the original images are shown and enlarged 16 times.

FIG. 8B is a grayscale picture of a three-color image of Rolony sequenced as described in Example I. Interrogation of the 9$^{th}$ (left image) and 15$^{th}$ positions (right image) downstream the sequencing primer site on the ssDNA template. Geometrical shapes as indicated in the legend mark Rolony that are common in both images. Base change between two positions can be observed by shape change. Only a small portion of the original images are shown and enlarged 16 times.

Figure 9A:
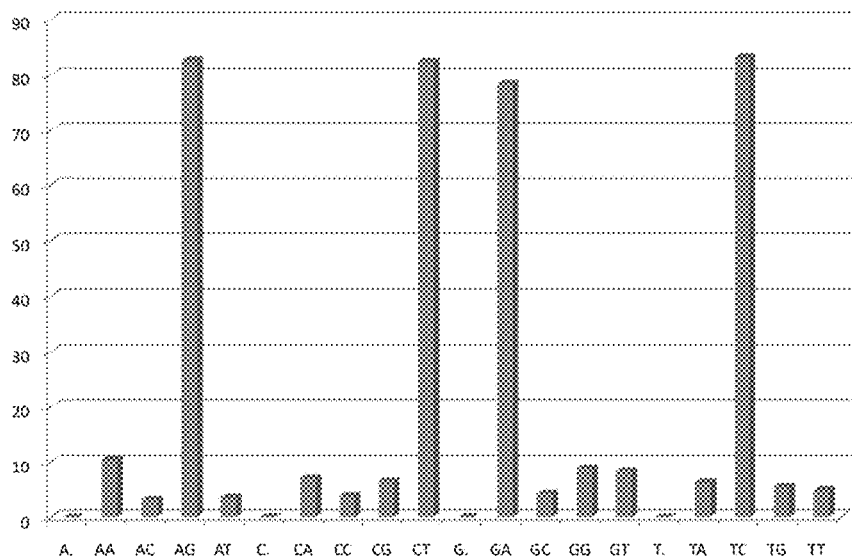
FIG. 9A is a histogram comparing proportion of base transition between the $3^{rd}$ and $9^{th}$ positions from Rolony sequenced as described in Example I. By example, based on the templates used in Example I, one would expect the majority of A (position 3 from the sequencing primer) to change to G (position 9).

FIG. 9A is a histogram comparing proportion of base transition between the 3$^{rd}$ and 9$^{th}$ positions from Rolony sequenced as described in Example I. By example, based on the templates used in Example I, one would expect the majority of A (position 3 from the sequencing primer) to change to G (position 9).

Figure 9B:
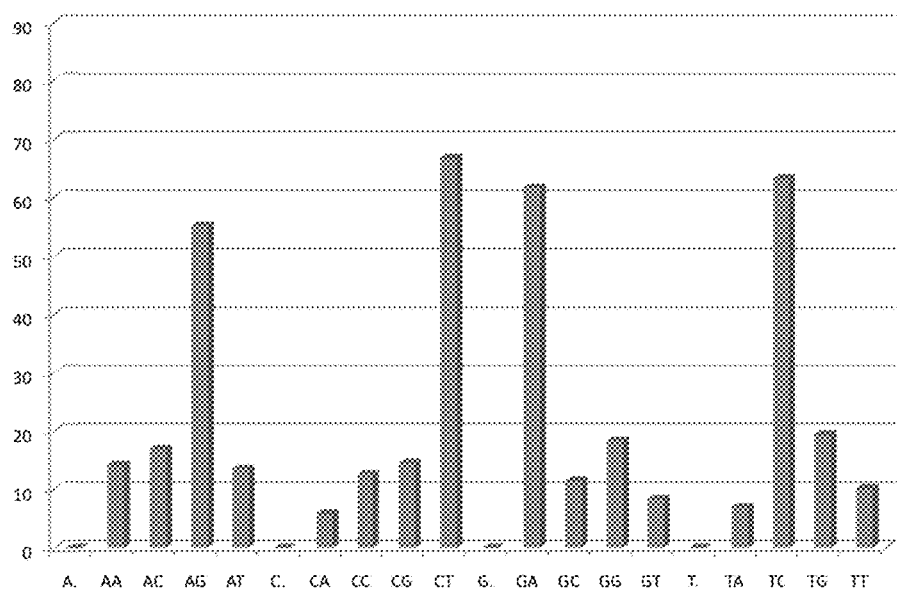
FIG. 9B is a histogram comparing proportion of base transition between the $9^{th}$ and $15^{th}$ positions from Rolony sequenced as described in Example I. By example, based on the templates used in Example I, one would expect the majority of G (position 9 from the sequencing primer) to change to A (position 15).

FIG. 9B is a histogram comparing proportion of base transition between the 9$^{th}$ and 15$^{th}$ positions from Rolony sequenced as described in Example I. By example, based on the templates used in Example I, one would expect the majority of G (position 9 from the sequencing primer) to change to A (position 15).

---

The invention claimed is:

1. A method for identifying two particular nucleotides at different positions in a target nucleic acid sequence of a target polynucleotide, comprising:
   (a) hybridizing a sequencing primer to a single stranded nucleic acid template derived from said target polynucleotide, wherein said single stranded nucleic acid template is immobilized to a support, and wherein said single stranded nucleic acid template comprises said target nucleic acid sequence;
   (b) hybridizing an oligonucleotide probe comprising (i) a template hybridizing nucleic acid sequence having a sequence that is complementary with said target nucleic acid sequence, and (ii) a template nonhybridizing nucleic acid structure that does not have a sequence that is complementary with said target nucleic acid sequence, to said single stranded nucleic acid template, thereby forming a hybridized complex comprising said single stranded nucleic acid template, said sequencing primer, and said oligonucleotide probe;
   (c) on said hybridized complex, ligating said template hybridizing nucleic acid sequence of said oligonucleotide probe to said sequencing primer, thereby forming an extended hybridized sequence,
      wherein said template nonhybridizing nucleic acid structure is attached to said template hybridizing nucleic acid sequence of said oligonucleotide probe, and
      wherein said template nonhybridizing nucleic acid structure comprises a plurality of probe hybridization sites comprising a plurality of pre-determined sequences, wherein each of the probe hybridization sites corresponds to one of specific nucleotides at one of specific positions of said oligonucleotide probe and the specific nucleotides are fully complementary to the target nucleic acid sequence;
   (d) subsequent to step (c), detecting a hybridization between a plurality of barcode probes and said plurality of pre-determined sequences on said hybridized complex wherein said plurality of barcode probes comprises a first set of barcode probes and a second set of barcode probes, and wherein said detecting a hybridization between a plurality of barcode probes and said plurality of pre-determined sequences comprises (i) hybridizing a first barcode probe from said first set of barcode probes to a first pre-determined sequence of said plurality of pre-determined sequences, (ii) removing said first set of barcode probes unhybridized to the first pre-determined sequence, (iii) identifying the hybridization between said first barcode probe and the first pre-determined sequence by detecting a detectable moiety of said first barcode probe, (iv) removing said first barcode probe hybridized to said first pre-determined sequence from said first pre-determined sequence, (v) hybridizing a second barcode probe from said second set of barcode probes to a second pre-determined sequence of said plurality of pre-determined sequences, and (vi) identifying the hybridization between said second barcode probe and the second pre-determined sequence by detecting a detectable moiety of said second barcode probe; and
   (e) determining identities of two of the specific nucleotides in the specific positions of said oligonucleotide probe based on hybridization results from step (d), thereby identifying the two particular nucleotides at the different positions in said target nucleic acid sequence of said target polynucleotide by the two of the specific nucleotides in the specific positions of said oligonucleotide probe.

2. The method of claim 1, wherein said oligonucleotide probe is a nucleic acid sequence having up to about 100 hybridizable nucleotides.

3. The method of claim 1, wherein said template nonhybridizing nucleic acid structure comprises a recognition site for a cleavage agent and said template nonhybridizing nucleic acid structure is removed by said cleavage agent to generate an extendable terminus on said extended hybridized sequence.

4. The method of claim 3, wherein said cleavage agent is a chemical reactant.

5. The method of claim 3, wherein said template nonhybridizing nucleic acid structure comprises photocleavable linkers which are cleavable by ultraviolet (UV) illumination between wavelengths of about 275 nanometers (nm) to about 375 nm.

6. The method of claim 1, wherein said template nonhybridizing nucleic acid structure is a stem and loop structure.

7. The method of claim 1, wherein said template nonhybridizing nucleic acid structure is a linear structure.

8. The method of claim 1, wherein said detectable moiety is optically detectable.

9. The method of claim 1, wherein said detectable moiety is a fluorescent marker or a luminescent marker.

10. The method of claim 1, wherein said template hybridizing nucleic acid sequence includes six nucleotides.

11. The method of claim 1, wherein the number of the probe hybridization sites on said template nonhybridizing nucleic acid structure is equal to the number of the specific nucleotides at the specific positions of said oligonucleotide probe.

12. The method of claim 1, further comprising removing said template nonhybridizing nucleic acid structure to generate an extendable terminus on said extended sequence.

13. The method of claim 12, further comprising, after said removing said template nonhybridizing nucleic acid structure, repeating steps (b) to (e) with an additional oligonucleotide probe having a template hybridizing nucleic acid sequence having a sequence that is complementary with said target nucleic acid sequence and a template nonhybridizing nucleic acid.

14. The method of claim 1, wherein said detectable moiety is selected from the group consisting of a radioactive moiety, enzyme, prosthetic group, fluorescent marker, luminescent marker, bioluminescent marker, metal particle, protein-protein binding pair, and protein-antibody binding pair.

15. The method of claim 1, further comprising removing said second barcode probe hybridized to said second pre-determined sequence from said second pre-determined sequence, hybridizing a third barcode probe from a third set of barcode probes to a third pre-determined sequence of said plurality of pre-determined sequences, identifying the hybridization between said third barcode probe and the third pre-determined sequence by detecting a detectable moiety of said third barcode probe, and determining identity of an additional nucleotide in a position of said oligonucleotide probe different from the two specific nucleotides in the specific positions of said oligonucleotide probe based on the hybridization between said third barcode probe and the third pre-determined sequence, thereby identifying an additional particular nucleotide at a position in said target nucleic acid sequence of said target polynucleotide different from the two particular nucleotides at the different positions in said target nucleic acid sequence of said target polynucleotide by the additional nucleotide in the position of said oligonucleotide probe different from the two specific nucleotides in the specific positions of said oligonucleotide probe.

* * * * *